US010379032B2

(12) United States Patent
Godfrey et al.

(10) Patent No.: US 10,379,032 B2
(45) Date of Patent: Aug. 13, 2019

(54) CALCULATING A COMPOSITION FOR A PREPARATION FOR TREATING HAIR FIBERS

(71) Applicant: The Procter & Gamble Company, Cincinnati, OH (US)

(72) Inventors: Simon Paul Godfrey, Oberursel (DE); Viktoriya Senduyreva, Frankfurt (DE); Gabriela Schaefer, Sarstedt (DE)

(73) Assignee: The Procter and Gamble Company, Cincinnati, OH (US)

( * ) Notice: Subject to any disclaimer, the term of this patent is extended or adjusted under 35 U.S.C. 154(b) by 5 days.

(21) Appl. No.: 15/704,440

(22) Filed: Sep. 14, 2017

(65) Prior Publication Data
US 2018/0080865 A1 Mar. 22, 2018

(30) Foreign Application Priority Data

Sep. 16, 2016 (EP) .................... 16189222

(51) Int. Cl.
*G01N 21/25* (2006.01)
*G06T 7/90* (2017.01)
(Continued)

(52) U.S. Cl.
CPC .............. *G01N 21/25* (2013.01); *G01J 3/42* (2013.01); *G01J 3/463* (2013.01);
(Continued)

(58) Field of Classification Search
CPC .. G01N 21/25; G01J 3/463; G01J 3/42; G01J 2003/466; G06T 19/20; G06T 15/50; G06T 15/04; G06T 7/90; G06T 15/80; G06T 2219/2012; G06T 2200/08; G06T 2207/10024; G06T 2207/30196; G06K 9/481; G06K 9/00208; G06K 9/4652; G06K 9/6215; A45D 2044/007
(Continued)

(56) References Cited

U.S. PATENT DOCUMENTS 9,205,283 B2 12/2015 Miklatzky et al.
9,844,687 B2 12/2017 Landa et al.
(Continued)

OTHER PUBLICATIONS

Zinke, Arno, et al. "A practical approach for photometric acquisition of hair color." ACM Transactions on Graphics (TOG). vol. 28. No. 5. ACM, (Year: 2009).*
(Continued)

*Primary Examiner* — Amandeep Saini
(74) *Attorney, Agent, or Firm* — Alexandra S. Anoff

(57) ABSTRACT

A method and apparatus for calculating a composition for a preparation for treating hair fibers. The method comprises: obtaining (330) a target specification, wherein the target specification comprises one or more numerical parameters defining a desired appearance of the hair fibers; providing (340) a first computational model that relates a composition of a preparation to a predicted appearance of the hair fibers when treated by that preparation; and calculating (350), using the first computational model and the target specification, a composition for the preparation that is predicted to produce, if the hair fibers are treated with the preparation, an appearance similar or identical to the desired appearance.

15 Claims, 7 Drawing Sheets

(51) Int. Cl.
*G06K 9/00* (2006.01)
*G06K 9/46* (2006.01)
*G06K 9/48* (2006.01)
*G06K 9/62* (2006.01)
*G06T 15/04* (2011.01)
*G06T 15/80* (2011.01)
*G06T 19/20* (2011.01)
*G06T 15/50* (2011.01)
*G01J 3/42* (2006.01)
*G01J 3/46* (2006.01)
*A45D 44/00* (2006.01)

(52) U.S. Cl.
CPC ....... *G06K 9/00208* (2013.01); *G06K 9/4652* (2013.01); *G06K 9/481* (2013.01); *G06K 9/6215* (2013.01); *G06T 7/90* (2017.01); *G06T 15/04* (2013.01); *G06T 15/50* (2013.01); *G06T 15/80* (2013.01); *G06T 19/20* (2013.01); *A45D 2044/007* (2013.01); *G01J 2003/466* (2013.01); *G06T 2200/08* (2013.01); *G06T 2207/10024* (2013.01); *G06T 2207/30196* (2013.01); *G06T 2219/2012* (2013.01)

(58) Field of Classification Search
USPC ........................................................ 382/141
See application file for complete search history.

(56) References Cited

U.S. PATENT DOCUMENTS

| | | | |
|---|---|---|---|
| 2014/0082854 A1* | 3/2014 | Landa | A45D 19/02 8/405 |
| 2015/0082553 A1 | 3/2015 | Landa et al. | |
| 2016/0110915 A1* | 4/2016 | Degenhard | G06T 15/506 703/2 |

OTHER PUBLICATIONS

Arno Zinke et al., "A practical approach for photometric acquisition of hair color", ACM Transactions on Graphics (TOG), ACM, US, vol. 28, No. 5, Dec. 1, 2009.

PCT International Search Report and Written Opinion for PCT/US2017/051779 dated Jan. 2, 2018.

* cited by examiner

CALCULATING A COMPOSITION FOR A PREPARATION FOR TREATING HAIR FIBERS

FIELD OF THE INVENTION

The present invention relates to methods and apparatus for calculating a composition for a preparation for treating hair fibers. The method is optionally followed by manufacturing the preparation having the calculated composition. Embodiments of the invention may be particularly relevant for formulating hair dye preparations—for example, designing a hair dye preparation to produce a particular desired shade.

BACKGROUND OF THE INVENTION

Formulating preparations for the treatment of hair fibers is a complex task. Taking hair dye preparations as an example, several challenges can be identified.

When the goal is to create a new hair dye preparation, to produce a new hair color (shade), the first challenge may be to actually define the desired shade. Traditionally, this has often been done by comparison with existing shades: "a bit like this one, but warmer/darker/lighter/more ash/less red/ etc." Obviously, this is a highly subjective and imprecise way to specify a desired shade. The person trying to specify the shade is usually not the person responsible for formulating the dye preparation, which can lead to difficulties in communicating and understanding the precise target shade. For example, a customer in a hair salon may be trying to explain a desired shade to a hair stylist or colorist. Or a hair stylist, colorist, or product developer may be trying to communicate a shade to a dye-formulation expert (usually a specialist chemist). This is further complicated due to the poor ability of humans to be able to accurately remember color. Hence even if a hair dye preparation is subsequently produced to deliver exactly the color initially described, it may be that the person who defined the desired shade no longer recognises it as being what they wanted, and request a different color to be produced, which again when they view the actual result of this new hair dye preparation differs again from what they thought they wanted.

Assuming that the target shade can be successfully defined and agreed, the next challenge is to formulate a composition for a dye preparation that will actually achieve this target shade. This is a non-trivial task because of the complex chemical processes involved in dyeing hair. The end result will depend on the chemical and physical interactions between the existing hair, the dye preparation, and the light illuminating the dyed hair. Treatment conditions (for example, temperature and time) will affect these interactions.

A dye formulation expert may choose the individual dye compounds and their concentrations to be used in a hair dye product. A hair stylist/colorist may choose one or more hair dye products and mix them with an oxidizing agent in suitable proportions to achieve a desired shade. Each hair dye product will typically contain several dye compounds. As used herein, in general, a "preparation" can include both a dye product such as may be formulated by a dye formulation expert, typically containing a plurality of dye compounds, and a mixture of such dye products, such as may be mixed together by a professional colorist.

Even with significant experience, it may be difficult for a dye formulation expert or professional colorist to design a dye preparation that achieves precisely the desired target shade. In particular, when developing a new dye preparation in a commercial setting, it is usual for a dye formulation expert to go through a highly iterative process—formulating a test product, testing it on hair, assessing the results and adjusting the formulation based on his/her skill and experience to approach the target shade. This is laborious, expensive, time consuming, inefficient, and inexact. A professional colorist may have more limited options for iteration, because there will usually be only one customer's hair on which to test a preparation and undesired results may need to be corrected by further dyeing. Therefore, colorists tend to take a conservative approach, recommending only incremental changes to hair color, in order to avoid unpleasant surprises and customer dissatisfaction.

In other instances, the goal is not to create a new shade, but to formulate a composition for a hair dye preparation that will achieve the same shade as an old dye preparation, by using different ingredients. This can happen when an existing ingredient becomes scarce, or expensive, or when safety and/or regulatory guidance change, requiring a current composition to be altered. Although the target shade may be easier to specify when it is the same as an old shade, the problems encountered in achieving that shade are the same as discussed above.

SUMMARY OF THE INVENTION

According to a first aspect, there is provided a method of calculating a composition for a preparation for treating hair fibers, the method comprising:

obtaining a first image of hair fibers;

creating a modified image, based on the first image, the modified image illustrating a desired appearance of the hair fibers;

deriving a target specification, based on at least one of: the modified image; and the modification performed to the first image, wherein the target specification comprises one or more numerical parameters defining the desired appearance of the hair fibers;

providing a first computational model that relates a composition of a preparation to a predicted appearance of the hair fibers when treated by that preparation; and calculating, using the first computational model and the target specification, a composition for the preparation that is predicted to produce, if the hair fibers are treated with the preparation, an appearance similar or identical to the desired appearance.

This method can simultaneously address the problems of specifying and achieving a target shade. The modified image can provide a principled, objective way to specify the target shade.

And the first computational model can provide a principled, automated approach to assist in designing a composition for the preparation that will achieved the target shade.

"Similar" to the desired appearance may mean at least locally optimized similarity, in the sense that any incremental change to the calculated composition will make the predicted appearance more different from the target, or at least will not reduce the difference between the predicted appearance and the target.

The first image may be an image of real hair fibers to be treated using the preparation. Alternatively, it may be a synthetic image derived from an image of real hair fibers to be treated.

The modified image may be created by performing a modification to the first image. Alternatively, it may be created by rendering a synthetic image based on the first image and performing a modification to the synthetic image.

Similarity (and difference, respectively) may be measured by color difference, for example a two or three-dimensional vector of color difference, such as a color difference in the CIE L*a*b* color space.

The modifications to the first image are preferably performed in response to user input. This can allow a user to specify a desired appearance, such as a target shade.

The step of performing a modification to the first image may comprise: providing a second computational model describing the interaction of light with hair fibers; obtaining, for the first image, a first set of hair fiber optical parameters, which describes the hair fibers in the first image; modifying the first set of fiber optical parameters, to produce a second set of hair fiber optical parameters describing a plurality of modified hair fibers; simulating, using the second computational model and the second set of hair fiber optical parameters, how light would interact with the modified hair fibers; rendering, based on the result of the simulation, a first synthetic image showing the appearance of the modified hair fibers; and providing said first synthetic image as the modified image.

This method can allow photorealistic images of hair fibers to be produced, because it can model the way in which light actually interacts with hair fibers. By starting with parameters that describe a plurality of hair fibers, and then modifying those parameters, the synthetic image can accurately represent the appearance of a modified version of the original hair fibers. And, because the modified parameters are still tied to the computational model, it can be ensured that the appearance of these modified fibers is—at least in principle—physically realizable. That is, it is possible for some fibers in the real world to have this appearance. In contrast, if a "real" image of the original fibers is modified directly, such as by using conventional image processing techniques, there is no confidence that the result will either look realistic, or will represent something that is physically realizable.

The step of simulating the interaction of light with the fibers may comprise calculating, using a processor, how light illuminating the modified fibers would be scattered and/or absorbed by those fibers. Scattering interactions may include at least one of: reflection and refraction.

In general, the parameters of the fibers used in the model are optical parameters, characterizing various aspects of the interactions between the fibers and incident light.

The interaction of light with the fibers may include at least one of (or any combination of two or more of) the following physical interactions: specular reflection; diffuse reflection; absorption; refraction; and transmission. As used herein, the term "scattering" refers to non-absorptive interactions between light and fibers.

Preferably, the first set of hair fiber parameters is obtainable by physical measurement and analysis of real hair fibers. That is, the parameters may be derived from actual hair fiber samples.

The modification of the first set of hair fiber parameters may represent or approximate a physical modification of the real fibers—for example, a treatment applied to the real fibers, such as a chemical treatment. The chemical treatment may comprise at least one of (or any combination of two or more of): a pigment, structural color, dye, polymeric dye, optical effect and bleaching.

The method may further comprise performing additional modifications to the image. Modifications may be performed in an iterative fashion to arrive at the desired appearance. In other words, the step of modifying, simulating, and rendering may be iterated until the synthetic image has the desired appearance.

The target specification may comprise the second set of hair fiber optical parameters. In the case of an iterative approach, the target specification may comprise the final set of hair fiber optical parameters, at the end of the iterations.

The method may further comprise displaying the first synthetic image, preferably on a color-calibrated monitor. If the synthetic image is rendered as a high dynamic range image, the dynamic range of the image may be reduced for display. For example, an 8-bit version of the synthetic image may be displayed—in particular, if the display screen is not capable of displaying high dynamic range images.

As used herein, a step of "displaying" an image preferably comprises displaying it on a display screen—that is, providing control signals to a display screen, to control the display screen to show the image. Preferably, the display screen is color-calibrated, for consistently accurate color reproduction. In some circumstances, an image may be displayed by other technical means. For example, an image may be displayed by printing—that is the step of "displaying" may comprise providing control signals to a printer, to control the printer to print the image. The printer is preferably color-calibrated.

In conventional strategies for the development of hair dye preparations, specifying the intended color can be a significant challenge. If a team of people is involved in the specification and dye formulation (as is usually the case), each person may have a different concept of the desired result. The consequence is that many iterations may be needed—with dye preparations being formulated, tested, and rejected because they do not match the desired result (as understood by one or more members of the team). Essentially, the early attempts at formulation are wasted, because they are being used to refine the understanding of what is desired, rather than trying to achieve a well-defined goal. By using a photorealistic synthetic image to specify the target color, the problems of natural language specification and subjectivity are avoided. The synthetic image provides an objective target. All of the people in the team can see, understand, and agree on the goal that is desired, or continue modifying that goal until a consensus is reached. This can dramatically reduce the number of iterations when formulating dye preparations, thereby reducing the time and cost. The team of people can also be located remotely from one another, because the synthetic image can be transmitted electronically and displayed to each person on an individual color-calibrated monitor, if so desired.

Because the synthetic image is generated using a computational model of interactions between light and fibers (which is faithful to the real physical interactions between actual light and actual material hair fibers), the synthetic image can be natural looking and the color of the hair as it appears in the image can be physically realizable—at least under the illumination used in the simulation/rendering. A set of synthetic images can also be used to present the appearance of the modified hair fibers under a variety of different illumination conditions. This can allow the people specifying the color to verify that it will look attractive in different environments.

Each of the first and second sets of hair fiber optical parameters preferably comprises parameters for at least three of the following four components: a first backward scattering component, describing how incident light is reflected from a first surface of a hair fiber; a first forward scattering component, describing how incident light is transmitted through the first surface of the hair fiber and a second surface of the hair fiber; a second backward scattering component, describing how incident light is transmitted through the first surface of the hair fiber, reflected from the second surface of the hair fiber, and transmitted through a third surface of the hair fiber; and an absorption component, describing how incident light is absorbed by the hair fiber.

The first, second, and third surfaces may be different parts of the same continuous surface—for example, if the hair fiber is modeled as a cylinder. The first backward scattering component may represent a reflection from an exterior surface of the hair fiber. The first forward scattering component may represent a first refraction as light enters the hair fiber at the first surface and a second refraction as the light exits the hair fiber at the second surface. The second backward scattering component may represent refraction as light enters the hair fiber at the first surface; an internal reflection at the second surface; and further refraction as the light exits the hair fiber at the third surface.

The step of obtaining the first set of hair fiber optical parameters optionally comprises: processing the first image to determine a set of estimated hair fiber optical parameters; simulating, using the second computational model and the estimated hair fiber optical parameters, how light would interact with hair fibers with the estimated parameters; computing an error metric comparing the result of the simulation with the content of the first image; updating the estimated hair fiber optical parameters, based on the error metric; iterating the steps of simulating, computing, and updating, until the estimated hair fiber optical parameters converge to stable values; and determining the first set of fiber optical parameters based on the converged estimated fiber optical parameters.

This can provide a type of "analysis-by-synthesis" approach to measuring the fiber parameters of real hair fibers. The parameters are derived iteratively, by simulating how light would interact with fibers assuming that they had the currently estimated parameters, and comparing the results of the simulation with the appearance of the real fibers. The parameters are then updated, and the simulation and comparison are performed again, to see if the new parameters match the real fibers better or worse. After several iterations, this approach can converge to a set of parameters that accurately models the real fibers. This approach can avoid the need for expensive specialist equipment (such as a gonioreflectometer) and a time- or labor-intensive measurement and analysis process. Preferably, the only "measurement" needed is to photograph the plurality of real fibers, producing a digital image. This has many advantages. For example, if the fibers comprise human hair, it may be possible to determine the fiber parameters of real hair from hair on a person's head, without the need to cut off a hair sample.

The image of the plurality of real fibers is preferably a high dynamic range image. This can allow more accurate results, in the estimation of the parameters.

The target specification preferably comprises a target color vector and wherein the step of deriving the target color vector preferably comprises: storing a plurality of sets of hair fiber optical parameters, each set describing real hair fibers of a different shade, and each set being associated with a color vector that was has been directly measured from the real hair fibers of that shade; identifying, among the stored sets of hair fiber optical parameters, the set that is most similar to the second set of hair fiber optical parameters, this set being designated as the nearest-neighbour set, the corresponding hair fibers being designated as the nearest neighbour hair fibers, and the associated color vector being designated as the nearest neighbour measured color vector; simulating, using the second computational model and the nearest-neighbour set of hair fiber optical parameters, how light would interact with the nearest neighbour hair fibers; rendering, based on the result of the simulation, a nearest neighbour synthetic image showing the appearance of the nearest neighbour hair fibers; deriving a nearest neighbour synthetic color vector from the nearest neighbour synthetic image; deriving a modified image color vector from the modified image; calculating a color difference between the nearest neighbour synthetic color vector and the modified image color vector; and deriving the target color vector based on the nearest neighbour measured color vector and said color difference.

The step of modifying the first set of hair fiber optical parameters may comprise modifying at least one parameter related to a color of the hair fibers, whereby the second set of hair fiber optical parameters describes hair fibers having a modified color.

Optionally, modifying at least one parameter related to the color of the hair fibers comprises modifying at least one parameter related to a reflection spectrum, transmission spectrum, or absorption spectrum of the fibers. The modification may change the amplitude of one of these spectra in its entirety, or may change the amplitude at some wavelengths only, thereby changing the wavelength dependence of the spectra. The modification may represent a change in at least one of (or any combination of two or more of): the lightness, chroma, hue, and color saturation of the fibers. Lightness, chroma, and hue may be defined in the same way as specified in the CIE LCH or L*a*b* color spaces. Color saturation may be defined in the same way as in the HSL or HSV color spaces or may be defined as chroma, C, normalized by lightness, L, in the LCH or L*a*b* color spaces.

Each of the first and second sets of hair fiber optical parameters may comprise parameters describing an average fiber; and the second computational model may describe respective individual fibers by combining the parameters of the average fiber with a random perturbation.

This can be a good way to approximate the variations found among natural fibers in the real world. Usually, no two fibers will be identical; however, maintaining a set of parameters for every individual fiber may be prohibitively complicated. The random perturbation may comprise modification of the average parameters by a pseudo-random noise component—for example, computing the sum or product of the average parameters with a pseudo-random variable.

The first synthetic image may comprise a plurality of pixels corresponding to a respective plurality of spatial positions in a virtual image plane, and simulating how light would interact with the modified fibers may comprise simulating, for each of a plurality of rays of light arriving at each position, a journey of the ray from a light source to the position, said journey including an interaction with one or more of the modified fibers, wherein the simulation comprises calculations performed in parallel by two or more computing devices, each computing device simulating, for each position, the journeys of a subset of the plurality of rays to that position.

Here, "parallel" means that one calculation begins before another ends.

The two or more computing devices may comprise two or more cores in the same microprocessor; two or more microprocessors (for example, connected by a bus) in the same computer; or two or more microprocessors in respective different computers (for example, connected by a network).

The step of rendering the first synthetic image may comprise calculating a pixel value by combining contributions to the pixel from the plurality of rays, and the method may comprise rendering and displaying a preliminary synthetic image before the simulation has completed, based on the contributions to each pixel from rays that have been simulated up to the current time.

Here "completing" a simulation refers to calculating an intended number of samples per pixel. Thus, in this case, the method comprises rendering and displaying a preliminary synthetic image, followed by continuing to calculate more samples for each pixel. The preliminary image will be an approximation to the final image, to be obtained after the full set of samples has been calculated. This can provide progressive rendering, whereby the image is initially displayed in relatively lower quality, after a first number of samples per pixel has been calculated, and then later displayed in relatively higher quality, after additional samples per pixel have been calculated.

The first set of hair fiber parameters optionally includes at least one parameter that has a different value for at least one of the following: different hair fibers among the plurality of hair fibers; and different parts of the same hair fiber. Likewise, the second set of hair fiber parameters optionally includes at least one parameter that has a different value for at least one of the following: different hair fibers among the plurality of hair fibers; and different parts of the same hair fiber.

For example, this can model different hairs on different parts of the same head having different optical properties (such as color or shine). Alternatively or in addition, it can model variations in optical properties (such as color or lightness) along the length of individual hairs, for some or all of the hairs—for example, a differently colored root, at an end of the hair fiber nearest to the scalp. It may be advantageous to include both kinds of variations to make the synthetic image more realistic and natural looking. As discussed already above, different colors may be characterized by differing lightness, chroma, hue, and/or color saturation.

The method may further comprise obtaining light source parameters for use with the model, which describe a light source; the method comprising simulating, using the second computational model, the light source parameters, and the second set of hair fiber parameters, how light from the light source would interact with the modified hair fibers, wherein the light source parameters comprise an omnidirectional image.

Such omnidirectional images are also known as "light probe" images. They record the incident illumination conditions at a particular point in space, from substantially all directions. When using a light probe image as a light source for the simulation, the light source can be modeled as a closed surface (typically a sphere) and the fibers modeled as being located within the surface and illuminated from the interior of the surface. Each point (or pixel) of the light probe image can be considered as a discrete light source. The omnidirectional image is preferably a high dynamic range image.

By simulating using different light probe images, a user can see how the fibers would appear under different illumination conditions. The set of different light probe images available for the user to choose from may include one or more of the following: indoor scenes, outdoor scenes, scenes from different parts of the world, scenes illuminated by natural light (sunlight), scenes illuminated by artificial light, and scenes containing a mixture of both artificial and natural illumination.

Preferably, the omnidirectional image is an image of a real physical scene captured by a real physical camera. Alternatively, the omnidirectional image may be a synthetic image, representing a virtual scene.

The method may further comprise obtaining head parameters for use with the model, which describe the positions of a plurality of hair fibers on a head, defining a hairstyle, the method comprising simulating, using the second computational model, the head parameters, and the second set of hair fiber parameters, how light would interact with hair fibers in the positions described by the head parameters.

The head parameters define a hairstyle—preferably including the position, orientation, and/or shape of each individual fiber on the head (or a part of the head). This may include at least 20,000 fibers, preferably at least 50,000 fibers, more preferably at least 75,000 fibers, to produce a realistic synthetic image. The head may be "virtual"—that is, not representing any real person's hair style—in particular, because of the difficulty of measuring the position of every individual hair on a human head. The head parameters may describe other features of the head, such as the appearance of a face, a skin color of the face or of a scalp, or the appearance of eyes, ears, or a mouth.

The preparation preferably comprises a plurality of dye compounds of one type present in respective dosages and wherein, in the step of calculating the composition using the first computational model, the dosages of all of the dye compounds of said type in the preparation are variable independently of one another, wherein said type is one of: primary dye compounds; coupler dye compounds; and direct dye compounds.

Optionally, the preparation comprises a plurality of primary dye compounds present in respective dosages and wherein, in the step of calculating the composition using the first computational model, the dosages of all of the primary dye compounds in the preparation may be variable independently of one another.

Alternatively or in addition, the preparation may comprise a plurality of coupler dye compounds present in respective dosages and wherein, in the step of calculating the composition using the first computational model, the dosages of all of the coupler dye compounds in the preparation may be variable independently of one another.

The preparation may comprise one or more direct dyes, preferably in addition to primary and coupler dye compounds. Direct dyes are a third class of dyes that may be used to achieve certain colors that are difficult or impossible to achieve using oxidative dyes. A direct dye may comprise a preformed dye that is adapted to adhere to the hair—in particular, the surface region of the hair. Preferably, in the step of calculating the composition using the first computational model, the dosages of any direct dyes in the preparation are variable independently of one another and independently of the other types of dye (primary and coupler).

According to a second aspect, there is provided a method of calculating a composition for a preparation for treating hair fibers, the method comprising:

obtaining a target specification, comprising one or more numerical parameters defining a desired appearance of the hair fibers;

providing a first computational model that relates a chemical composition of the preparation to a predicted appearance of the hair fibers when treated by that preparation; and calculating, using the first computational model and the target specification, a composition for the preparation that is predicted to produce in the hair fibers an appearance similar or identical to the desired appearance, wherein the preparation comprises a plurality of dye compounds of one type present in respective dosages and wherein, in the step of calculating the composition using the first computational model, the dosages of all of the dye compounds of that type in the preparation are variable independently of one another, wherein said type is one of: primary dye compounds; coupler dye compounds; and direct dye compounds.

This method can address the problem of specifying a target shade by defining it with numerical parameters. It can address the problem of achieving that target shade by freeing the computational model of some of the constraints that have sometimes been imposed. The present inventors have recognized that selecting the dosages or concentrations of primary dyes or coupler dyes (or both) independently of one another can increase the possible shades that can be achieved. By doing this in the context of a computational model, and automating the calculation of the composition, the resulting increase in complexity is not prohibitive.

Independently variable means that the dosage or concentration of each dye compound of the same type is a free parameter, which does not have a fixed value or a fixed relationship with any of the other dosages for dye compounds of the same type. In other words, dye compounds of the same type can be mixed in any proportions—no two (or more) compounds of the same type need to be in fixed proportion to one another.

Preferably the dosages of all of the primary dyes are variable independently of one another and the dosages of all of the coupler dyes are variable independently of one another.

The preparation may comprise a plurality of primary dye compounds and a plurality of coupler dye compounds. A primary dye compound is one that is oxidized prior to reaction with a coupler, and a coupler dye compound is one that reacts with one or more of the oxidized primary dye compounds.

Preferably, the combined molar concentrations of all of the coupler dye compounds are sufficient to react with the combined molar concentrations of all of the primary dye compounds present in the preparation. This can avoid undesired reactions in which the primary dyes react with one another or with themselves. Thus, there may be fixed proportional relationships (or at least fixed minimum proportions) between the dosages of the primary dye compounds and those of the coupler dye compounds.

The preparation may comprise one or more direct dyes, preferably in addition to primary and coupler dye compounds. Direct dyes are a third class of dyes that may be used to achieve certain colors that are difficult or impossible to achieve using oxidative dyes. A direct dye may comprise a preformed dye that is adapted to adhere to the hair—in particular, the surface region of the hair. Preferably, in the step of calculating the composition using the first computational model, the dosages of any direct dyes in the preparation are variable independently of one another and independently of the other types of dye (primary and coupler).

Optionally, the step of calculating the composition for the hair-treatment preparation may further comprise calculating an amount or concentration for at least one compound which alters the level of melanin or formed dyes within the hair due to the preparation in order to achieve the desired appearance of the hair fibers.

Melanin bleaching is typically used in conjunction with oxidative dyes (that is, primary and coupler dyes). It may also be used with preparations that comprise direct dyes but no oxidative dyes. Often, the melanin bleaching compounds are provided within the preparation that is applied to the hair which also contains the primary and coupler dye compounds. However, in some cases a bleaching preparation is applied prior to regular hair coloring to deliver a dramatic change in melanin level prior to coloring. Therefore, the bleaching compounds can either be considered to be separate from the "preparation" or, considered as comprised within the "preparation" depending on the result that is trying to be achieved.

Preferably, the independently variable dosages referred to above are continuously variable.

The step of calculating the composition using the first computational model optionally comprises: calculating a plurality of candidate compositions, each of which is predicted to produce in the hair fibers an appearance similar or identical to the desired appearance; and choosing one of the candidate compositions, based on a criterion other than similarity to the target specification.

There may be several different possible compositions of the preparation, which would all produce the same result (for example, target shade). The first computational model can enable more than one candidate to be found, and a choice can then be made based on other criteria.

The criterion may comprise at least one, or any combination of two or more, of: a cost of manufacturing the preparation; a toxicological profile of ingredients within the preparation; a permanence of the result of treatment by the preparation, in particular a resistance to degradation due to at least one of: light at visible wavelengths, ultra-violet light, sweat, and water; a solubility of the preparation; an ionic strength of the preparation; a rheology of the preparation; a stability of the preparation; a coverage of the preparation on grey hair; an extent to which the preparation will stain the skin during treatment; an ability of the preparation to deliver uniform color from a root to a tip of hair fibers; an ability to tailor the penetration depth of the color delivered by the preparation; and a shine after application of the preparation.

Stability means the ability of the preparation to deliver acceptable performance—for example, in terms of color, rheology, and appearance—over the shelf life of the product, which is typically about three years.

Where the preparation is a hair dye, permanence may relate to a color-fastness of the dye—for example, a number of washes (or other suitable measure of exposure) before the dyed color fades.

Where the preparation is a hair dye, coverage of the preparation to grey hair may relate to the ability of the preparation to provide the visual appearance of removing grey hairs in a hair which comprises a mixture of white and pigmented hair.

The method optionally further comprises: before the step of calculating the composition using the first computational model, receiving one or more constraints on the composition; and in the step of calculating the composition, calculating a composition that satisfies the one or more constraints.

The constraints may include specific active ingredients to be used or not to be used or specific maximum or minimum concentrations of active ingredients. This can be used to reduce the search space by implicitly excluding at the outset compositions that would be undesirable for some reason. This may also help to simplify the chemistry of the composition by controlling the number of dye compounds, for example. It may also help to simplify the calculation of the composition.

The method optionally further comprises the steps of: making a preparation having the calculated composition; treating a sample of hair fibers with the preparation; comparing the treated hair fibers with at least one of: the target specification, and the modified image; modifying the target specification based on the result of the comparison; and calculating, using the first computational model and the modified target specification, a modified composition for the preparation.

This provides for iterative refinement of the composition, so that the result of treatment using the preparation more closely matches the target specification.

The iterative refinement is preferably automatic or at least semi-automatic, as summarized above.

Preferably, the step of comparing comprises measuring a color difference between the target specification and the treated hair fibers; and modifying the target specification based on the measured color difference.

For example, if the target specification comprises a color vector in a 3-D color space, the color difference may be measured in the same 3-D color space. The step of comparing may comprise firstly measuring a representative color vector for the treated hair fibers. This may involve capturing an image of the treated hair sample, followed by processing the image to extract the representative 3-D color vector. Alternatively, it may involve measuring a reflectance spectrum of the treated hair fibers using a spectrophotometer, followed by deriving the representative color vector from the measured reflectance spectrum. In both cases, the step of measuring the difference may then comprise subtracting the representative color vector for the treated hair fibers from the target color vector (or vice versa).

In the step of modifying the target specification, the color difference may be added to (or subtracted from, as appropriate) the previous target color vector, to produce the modified target color vector. The modified composition is then calculated based on this modified target, using the first computational model in the same way as in the initial iteration, as summarized above. In the subsequent iteration, when a sample of hair fibers is treated with a preparation having the modified composition, it is hoped that the treated fibers should more closely match the target color vector. In other words, the color difference is preferably reduced. In this way, the process can iteratively converge on a modified composition which best matches the target color vector.

In some embodiments, the color difference between the target specification and the treated hair fibers can be measured by rendering a synthetic image using the second computational model. This may comprise obtaining the hair fiber optical parameters of the treated sample of hair fibers and rendering a synthetic image using these parameters. This synthetic image can then be processed to extract a representative color vector. An advantage of extracting the representative color vector from a synthetic image, rather than from a real, captured image of the treated hair fibers is that the synthetic image can be rendered under a standard, controlled (virtual) illuminant, avoiding bias in the color vector due to real illumination. It may be easier to control the "virtual" illumination in the second computational model than it is to control the illumination of the real treated sample of hair fibers.

In some alternative embodiments, the comparison and modification steps may be performed by a human operator. The operator visually compares the treated sample of hair fibers with the modified image—in other words, he/she subjectively assesses the difference in appearance between the two. Then, the operator manually adjusts the target specification to account for any perceived difference. For example, if the operator considers that the treated sample is "too red" he/she may provide user input to reduce the "redness", either to directly modify the target specification (for example, target color vector) or to modify the image, from which a modified target specification can be derived.

The first computational model preferably includes at least one, or any combination of two or more, of: a computational component that describes mass transport of a preparation into hair fibers; a computational component that relates time-dependent concentrations of chemical species in a preparation to the initial composition of the preparation; a computational component that relates time-dependent concentrations of chemical species in hair fibers to time-dependent concentrations of chemical species in the preparation; and a computational component that relates concentrations of chemical species to a reflectance spectrum of hair fibers.

The target specification preferably comprises one of: a three-dimensional vector specifying a color in a three dimensional color space; and a reflectance spectrum, preferably a physically measured real reflectance spectrum.

Preferably the target specification is a vector in the L*a*b* (CIELAB) color space.

Using a reflectance spectrum as the target specification may have the advantage that the target spectrum can be independent of the light source used to illuminate the hair.

The step of deriving a target specification from the modified image may comprise extracting an L*a*b* value from the modified image.

Optionally, the preparation comprises a hair dye and the desired appearance of the hair fibers is a desired color.

The preparation preferably comprises at least one primary dye, at least one coupler dye, an alkali, and optionally at least one direct dye. When used to treat hair, the preparation will typically be mixed with another preparation containing an oxidant, such as hydrogen peroxide. This additional preparation is also known as a developer and mixing is preferably performed immediately before application to the hair.

In other words, typically, the "preparation" whose composition is calculated according to an embodiment of the invention (and which is then made and sold) will not include any oxidant. This product may be referred to as the "tint". Optionally, however, a quantity or a concentration of an oxidant can also be calculated using the first computational model. Also optionally, the "preparation" whose composition is calculated may comprise the oxidant—for example, in some circumstances, the "preparation" may refer to the final mixed product actually applied to the hair.

Details of the second aspect, as summarized above, are also applicable to the first aspect of the invention and may be combined with details of the first aspect.

Also provided is/are one or more processor-readable storage devices containing processor readable code for programming one or more processors to perform a method according to any preceding claim.

In particular, there is/are provided one or more processor-readable storage devices containing processor-readable code for programming one or more processors to perform a method of calculating a composition for a preparation for treating hair fibers, the method comprising the steps of: obtaining a first image of hair fibers; creating, based on the first image, a modified image illustrating a desired appearance of the hair fibers; deriving a target specification, based on at least one of: the modified image; and a modification that was performed to the first image to create the modified image, wherein the target specification comprises one or more numerical parameters defining the desired appearance of the hair fibers; providing a first computational model that relates a composition of a preparation to a predicted appearance of the hair fibers when treated by that preparation; and calculating, using the first computational model and the target specification, a composition for the preparation that is predicted to produce, if the hair fibers are treated with the preparation, an appearance similar or identical to the desired appearance.

Also, there is/are provided one or more processor-readable storage devices containing processor-readable code for programming one or more processors to perform a method of calculating a composition for a preparation for treating hair fibers, the method comprising the steps of: obtaining a target specification, comprising one or more numerical parameters that define a desired appearance of the hair fibers; providing a first computational model that relates a chemical composition of the preparation to a predicted appearance of the hair fibers when treated by that preparation; and calculating, using the first computational model and the target specification, a composition for the preparation that is predicted to produce in the hair fibers an appearance similar or identical to the desired appearance, wherein the preparation comprises a plurality of dye compounds of one type present in respective dosages and wherein, in the step of calculating the composition using the first computational model, the dosages of all of the dye compounds of that type in the preparation are variable independently of one another, wherein said type is one of: primary dye compounds; and coupler dye compounds; and direct dye compounds.

A storage device (or, equivalently, storage medium) may be non-transitory.

Also disclosed is a method of making a preparation for treating hair fibers, the method comprising: calculating a composition of the preparation according to a method as summarized above; followed by making the preparation having the calculated composition.

Additionally disclosed is a method of making a preparation and using it to treat hair fibers, the method comprising: calculating the composition of the preparation according to a method as summarized above; followed by making the preparation having the calculated composition; and applying the preparation to hair fibers.

Making the preparation may comprise manufacturing it, for example on a large scale using mass production processes. Alternatively, the step of making the preparation may be performed in a salon or store.

When applying (or shortly before applying) the preparation to hair fibers, to treat them, it may be mixed with a developer containing an oxidant such as hydrogen peroxide.

BRIEF DESCRIPTION OF THE DRAWINGS

Examples of the invention will now be described in detail with reference to the accompanying drawings, in which.

DETAILED DESCRIPTION OF THE INVENTION

Figure 1:
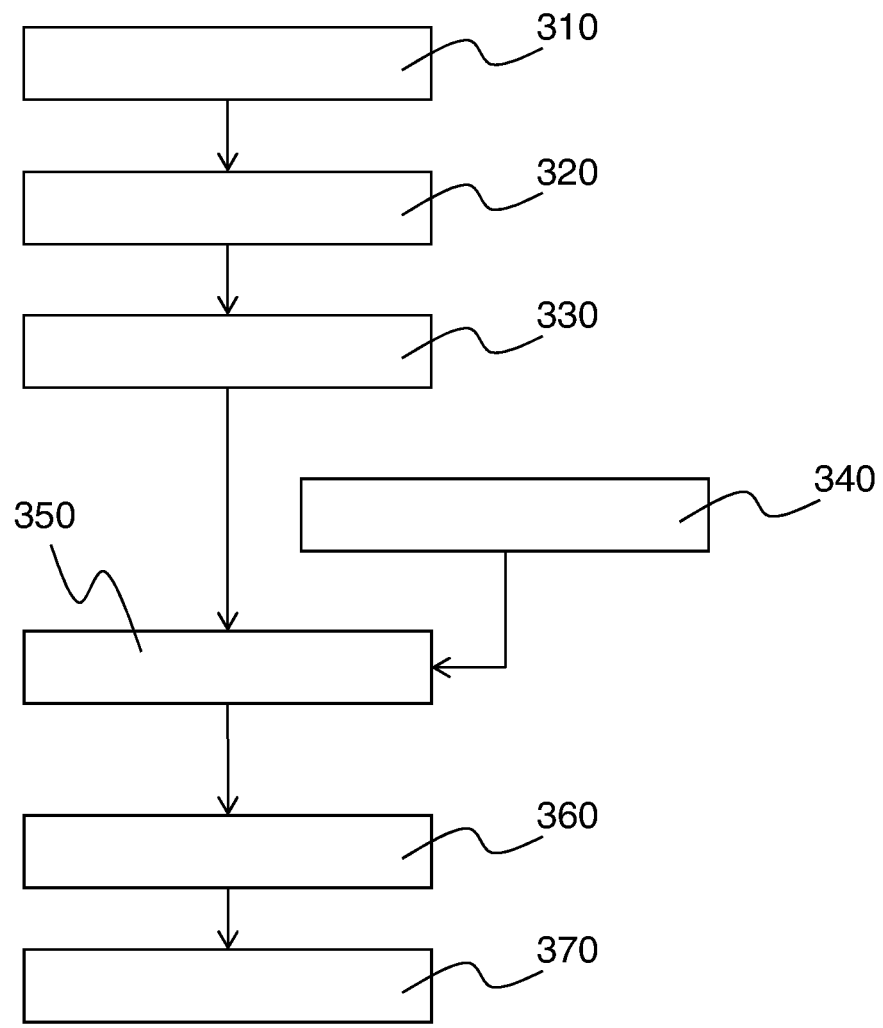
FIG. 1 is a flowchart illustrating a method of calculating a composition for a preparation for treating hair fibers according to an embodiment.

The following patent applications will be referred to in the description below, to ensure a clear, concise, and complete explanation of exemplary embodiments of the invention, while avoiding unnecessary repetition of details that have been disclosed previously in other contexts. These applications are hereby incorporated by reference in their entirety: European patent application number 14189661.3, filed 21 Oct. 2014; and international application number PCT/US2013/027268, filed 22 Feb. 2013 (international publication number WO 2013/126657).

As used herein, the term optically correct or photorealistic refers to an image which accurately portrays the interaction of visible electromagnetic radiation with a fibrous structure of particular optical properties.

As used herein the term color correct refers to an image which accurately portrays a fibrous structure of particular optical properties illuminated by a visible electromagnetic radiation source having a particular emissive spectrum.

As used herein the term fibrous structure refers to any structure comprised of discrete strands or fibers. Fibers may be artificial or natural fibers. In particular the term may be used to refer to an array of strands of keratinous materials. Keratinous fibers may be selected from wool, fur, silk, hair and mixtures thereof; preferably from mammalian hair; more preferably from human hair. Hair may be living hair (that is, on a living body) or non-living hair (that is, in a wig, hairpiece, or other aggregation of non-living keratinous fibers). Hair may be from Caucasian, Asian, African, Afro-Caribbean origins or combinations of these ethnic types. Hair may be selected from untreated hair, treated hair, and mixtures thereof. Treated hair may be selected from artificially-colored hair, bleached hair, permanently-waved hair, and mixtures thereof.

The fibers may have an average diameter from about 10 to about 200 microns, preferably from about 30 to about 150 microns, more preferably about 50 to about 120 microns.

As used herein, "high" dynamic range refers to images with a bit-resolution of more than 8 bits per pixel per color channel or more than 24 bits per pixel in total for a color image. Ordinary digital images typically use 8 bits per pixel, per color channel and therefore 24 bits per pixel to represent a conventional color image. Preferably, a high dynamic range image has at least 10 bits per pixel per color channel.

As used herein, light refers to electromagnetic radiation in the visible spectrum.

As used herein, an omnidirectional image is one whose visual field includes 360 degrees in a first plane and at least 180 degrees in a second, orthogonal plane. This means that the field of view is effectively at least a hemisphere. Preferably, an omnidirectional image has a visual field including 360 degrees in both the first and second planes, such that the field of view is effectively a sphere.

As used herein, color-calibrated means that the color temperature, brightness, and color space is defined and then calibrated versus at least one reference color.

As used herein, a "preparation" is a substance that can be used to treat hair. The "composition" of the preparation refers to the ingredients from which the preparation is made and the relative proportions of those ingredients. Calculation of the composition can comprise selecting ingredients, selecting their relative proportions, or preferably both.

FIG. 1 shows a method of calculating a composition for a preparation for treating hair fibers, according to an embodiment. In this embodiment, the preparation comprises a hair dye. Aspects of the present invention can be used particularly advantageously to derive compositions for hair dyes and so this is a convenient example with which to explain the invention; however, the scope of the invention is not limited solely to hair dyes. In the example of FIG. 1, the method will be used to assist in dye formulation for a hair dye product to be mass produced and sold to professionals (such as hair stylists or colorists) or sold in retail outlets to consumers. Again, it will be understood that the scope of the invention is not limited to this.

Figure 2:
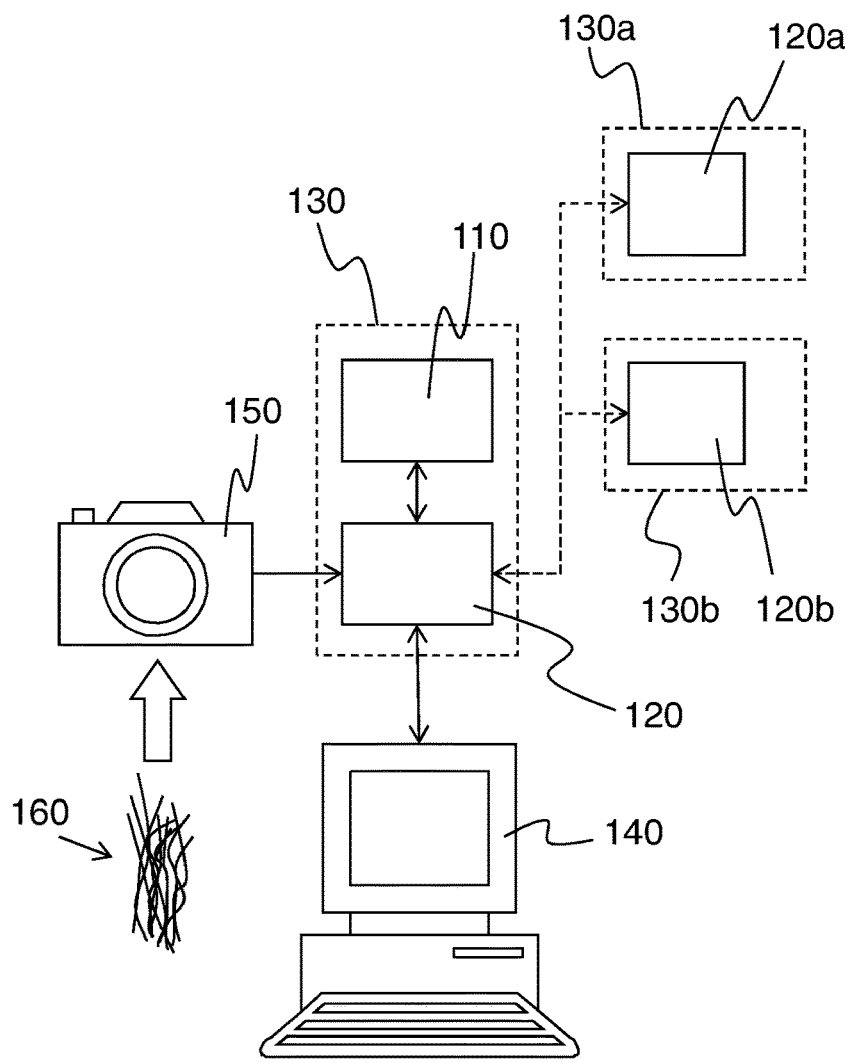
FIG. 2 shows an image processing apparatus for implementing the method of FIG. 1.

FIG. 2 shows an image processing apparatus for implementing the method of FIG. 1. The apparatus comprises a computer 130; a display screen 140; and a camera 150. The computer 130 comprises a memory 110 and a processor 120. The processor 120 and memory 110 are coupled to one another and configured to communicate with one another (for example, using an internal bus of the computer 130). The display screen 140 and the camera 150 are coupled to the computer 130 (for example, using wired or wireless connections) and configured to communicate with the processor 120. The apparatus further comprises two additional computers: a first computer 130a and a second computer 130b. These additional computers are coupled to the computer 130 via a network and are configured to communicate with the processor 120 across that network. Each computer 130a, 130b comprises a respective processor 120a, 120b. As will be explained in greater detail below, the two computers 130a and 130b may be used to assist in calculations by implementing parallel processing. The camera 150 can be configured to obtain an image of a plurality of real fibers 160 and to communicate this image to the processor 120 of the computer 130. The camera preferably comprises a high dynamic range digital camera. An exemplary camera is the TXG50c available from the Baumer Group, of Frauenfeld, Switzerland, and having a dynamic range of 12 bits for each of the Red, Green and Blue channels. A digital camera of lower dynamic range (for example, 8 bits per channel) may be used, by capturing multiple images at different exposures and combining them into a single high dynamic range image. The display screen 140 is configured to receive from the processor 120 control signals to control the display screen to display images. The display screen 140 is preferably color-calibrated.

In step 310 of the method of FIG. 1, the processor 120 obtains a first image of hair fibers. This first image can be obtained from the camera 150. For example, the first image may be an image of hair fibers on the head of a human model (in vivo sample), or it may be an image of a tress of hair that is used to define a particular standard hair type or color (in vitro sample). The first image shows the original color of the hair fibers. Preferably, the hair in the image is bent, so that the image captures the appearance of the hair from a plurality of different angles at the same time. An exemplary method and apparatus for capturing an image of hair (suitable for measuring its optical properties) is disclosed in EP 14189661.3.

Alternatively, the first image may be a synthetic image. Such a synthetic image may be derived from an image of real hair fibers, by analyzing the properties of the hair fibers in the original image. In some embodiments, an advantage of using a synthetic image is that the illumination can be more easily controlled in the synthetic image, allowing the subsequent method to be less sensitive to the effects of illumination in the original image.

In step 320, the processor 120 performs a modification to the first image, to create a modified image illustrating a desired appearance of the hair fibers. In this embodiment, the desired appearance of the hair fibers is a desired color (target shade). The processor may modify the image in response to user input. In this way, a user can manipulate the first image to define the target shade. The image can be manipulated in a variety of ways. The modification may comprise adjustment in a conventional color space, such as L*a*b* to change the color of the hair fibers in the image. Alternatively, more complex modifications are possible. An example of such modifications will be described in greater detail later below, with reference to FIG. 6. There may be more than one iteration of modification and more than one type of modification. For example the user may firstly manipulate the image by providing user input to the computer 130 (optionally in a series of iterations) to adjust a lightness value. Once happy with the lightness, the user may manipulate the image by providing user input to the computer 130 (optionally in a series of iterations) to adjust a hue or chromaticity of the hair.

Once the user is satisfied with the target shade illustrated in the modified image, the method proceeds to step 330 and the processor derives a target specification. This can be done based on the modified image, or the modification(s) that have been performed to the first image, or both. The target specification comprises one or more numerical parameters that define the desired appearance (target shade) of the hair fibers. In one example, a target specification can be derived from the modified image by calculating an average L*a*b* color vector value of the hair in the modified image.

In step 340, a computational model is provided, which relates a composition of a preparation to a predicted appearance of the hair fibers after they have been treated by that preparation. This model may be stored in the memory 110 and provided to the processor 120 during an initialization phase of the method. Details of the computational model will be discussed in greater detail below. The computational model enables the computer 130 to predict, for a given hair dye preparation having a given composition, what color the preparation will produce when used to treat the hair fibers.

In step 350, the processor calculates, using the first computational model and the target specification, a suitable composition for the preparation that is predicted to produce (or at least closely approximate) the target shade, when the hair fibers are treated with the preparation.

In step 360, the preparation having the calculated composition is made. This may be done manually or by machine. For example, when prototyping a new hair dye preparation to be sold to salons or to retail customers, a chemist in an industrial laboratory may make a small quantity of the dye preparation by hand, for testing. Later, when the prototyping process is complete, the final dye preparation may be mass produced in large quantities (for example, using known industrial chemical processes). In another example, the dye preparation may be a bespoke product for an individual customer in a hair salon. In this case, the preparation may be mixed by hand by a colorist, using the recipe calculated by the first computational model. To facilitate this, the apparatus may further comprise a dispensing unit, which allows the ingredients to be dispensed in an automated way. The dispensing unit would be configured to dispense defined amounts of dye compounds, according to the composition calculated in step 350. These would then be mixed manually by the colorist/stylist to produce a uniform product. An advantage of mixing manually is that the mixed preparation does not need to come into contact with the dispensing unit or other parts of the automated apparatus. It can be mixed in a separate mixing bowl, which can be cleaned or disposed of easily by the colorist/stylist.

As an alternative, the apparatus may optionally further comprise a mixing unit in addition to the dispensing unit. The mixing unit may be configured to mix the dye compounds dispensed by the dispensing unit, so as to make the preparation directly within the apparatus, without the need for manual mixing.

In step 370, the preparation made in step 360 is applied to hair fibers. To the extent that the first computational model is accurate, this should produce the desired appearance in the hair fibers. In other words, in the present example, the dye preparation should color the hair to produce the target shade.

An exemplary first computational model for use with the method of FIG. 1 will now be described, with reference to FIG. 3. The first computational model can include a computational component 410 that describes mass transport of individual components within the preparation into hair fibers; a computational component 420a that relates time-dependent concentrations of chemical species in the preparation to the initial composition of the preparation; a computational component 420b that relates time-dependent concentrations of chemical species in hair fibers to time-dependent concentrations of chemical species in the preparation; and a computational component 430 that relates concentrations of chemical species to a reflectance spectrum of hair fibers. The output 440 of the model is a prediction of the appearance (in this case, color) of the hair fibers after treatment by the preparation. In greater detail, the computational component 420a describes dye chemical reactions within the hair fibers; while computational component 420b describes oxidant reactions with melanin in the hair fibers. Computational component 430 comprises a list of chemical species and their respective concentrations, together with color information about each species. Each of the components will be described in greater detail below.

The process of color formation within hair, and the resulting appearance that is observed as a consequence of the application of an oxidative hair color product after a given period of time is complex.

Within an oxidative hair dye preparation a mixture of at least one "primary" and at least one "coupler" dye are present, together with an oxidant, and an alkali. The primary dye is oxidized by the oxidant to form an active intermediate. This in itself may be a multistep process with complex reaction kinetics. The active intermediate can then in turn subsequently react with the coupler, to form a leuco dye, which after undergoing another chemical oxidation produces the so called formed dye. The primary and coupler dyes are typically colorless, whereas the formed dye produces a characteristic color. Different primary and coupler dyes can produce different colors, and the observed color of the mixture of formed dyes is caused by a form of summation of the individual primary/coupler combinations. Further, for many combinations of primary and coupler the reactions may lead to the formation of more than one structural isomer as the resulting formed dye. Additionally some couplers may react only with a single primary dye, whereas others may be capable of reacting with two primary dyes.

Therefore, predicting the color formed within a solution of such dyes is complex, and the result of many simultaneous competing reactions.

However, the reactions do not occur within a simple solution, rather productive color formation occurs within the hair structure itself. Hair is typically considered to comprise two to four main structural components. Around the outside of a cross section of hair, are cuticle cells which are mostly transparent and which are present as a series of layers, and are orientated from root to hair tip. Within the cuticles is the cortex which is formed from cortical cells, and which provides the hair with the majority of its tensile strength. Within the cortex region are optionally pigments, melanin granules which may comprise eumelanin or pheomelanin or both at different absolute levels. The melanin provides hair with the majority of the observed pigment (color) variation in natural hair. Finally, in some hair fibers there is a medulla region which is a low density region within the hair. The color forming reactions of interest within hair color occur beneath the surface of the hair, in the cortex and within the cuticle cells. Therefore the mass transport as a function of time is preferably accounted for in predicting the color present within the fiber as a function of treatment time.

Additionally the presence of an oxidant, together with reaction conditions comprising a high pH can lead to changes in the melanin which is present within the hair fiber. This also needs to be considered when predicting the resulting color transformation after product application.

Once the concentrations of the various different chemical species are sufficiently well understood, the relationship between these and a light source, and observer (an individual's eyes or a color measurement) can be used to provide a color prediction of a given application of the preparation.

The computational component 410 describing mass transport will now be discussed.

A hair fiber can be approximated as a cylinder, for the purposes of modeling the transport of chemical species into the fiber. Various expressions are known for describing the diffusion of species into cylinders. These can be used to predict the amount of a given dye species within the hair, as a function of time. Many expressions may be used to describe this process mathematically, which may start with the basic diffusion equation expressed in radial terms $$\frac{\partial C}{\partial t} = \frac{1}{r}\frac{\partial}{\partial r}\left(rD\frac{\partial C}{\partial r}\right)$$

Where t is the time of the diffusion process, r is the radius of the cylinder, D is the diffusion coefficient and C is the concentration of a given dye.

Although it might not be practical to solve this equation exactly in all circumstances, various approaches exist to provide expressions which depend on the specified boundary conditions. One solution that may be of use is based on the following boundary conditions. A hair cylinder of radius a is placed within a volume of product A. The concentration of the dye within the product is initially $C_0$ and the hair itself initially contains no dye species. The concentration of dyes within the product (outside the hair fiber) is assumed to remain homogeneous throughout the process. This is equivalent to assuming that the diffusion within the product is much faster than the diffusion into the hair. Thus, it is assumed that the product does not become locally depleted of the dye species, near to the surface of the hair. The total amount of dye $M_t$ within the hair after time t is expressed as a fraction of the corresponding amount $M_\infty$ after infinite time by the following expression:

$$\frac{M_t}{M_\infty} = 1 - \sum_{n=1}^{\infty} \frac{4\left(\frac{A}{\pi\alpha^2 K}\right)\left(1 + \frac{A}{\pi\alpha^2 K}\right)}{4 + 4\left(\frac{A}{\pi\alpha^2 K}\right) + \left(\frac{A}{\pi\alpha^2 K}\right)^2 q_n^2} e^{\left(\frac{-Dq_n^2 t}{a^2}\right)}$$

Where K is the partitioning factor of the given dye between the hair and the product, and where $q_n$ are the positive non-zero roots of $$\left(\frac{A}{\pi\alpha^2 K}\right) q_n J_0(q_n) + 2J_1(q_n) = 0$$

Where $J_0$ and $J_1$ are Bessel functions and where $$\frac{M_\infty}{AC_0} = \frac{1}{1 + \frac{A}{\pi\alpha^2 K}}$$

Other assumptions can be made, which lead to alternative expressions to predict the amount of a given dye within the hair over time. Such expressions may further include terms that take into account the effect of the subsequent reaction of the dye species within the hair, which will further perturb the instantaneous concentration gradient across the product and hair.

The computational component 420a which predicts the chemical concentrations of dye compounds will now be discussed.

Figure 4:
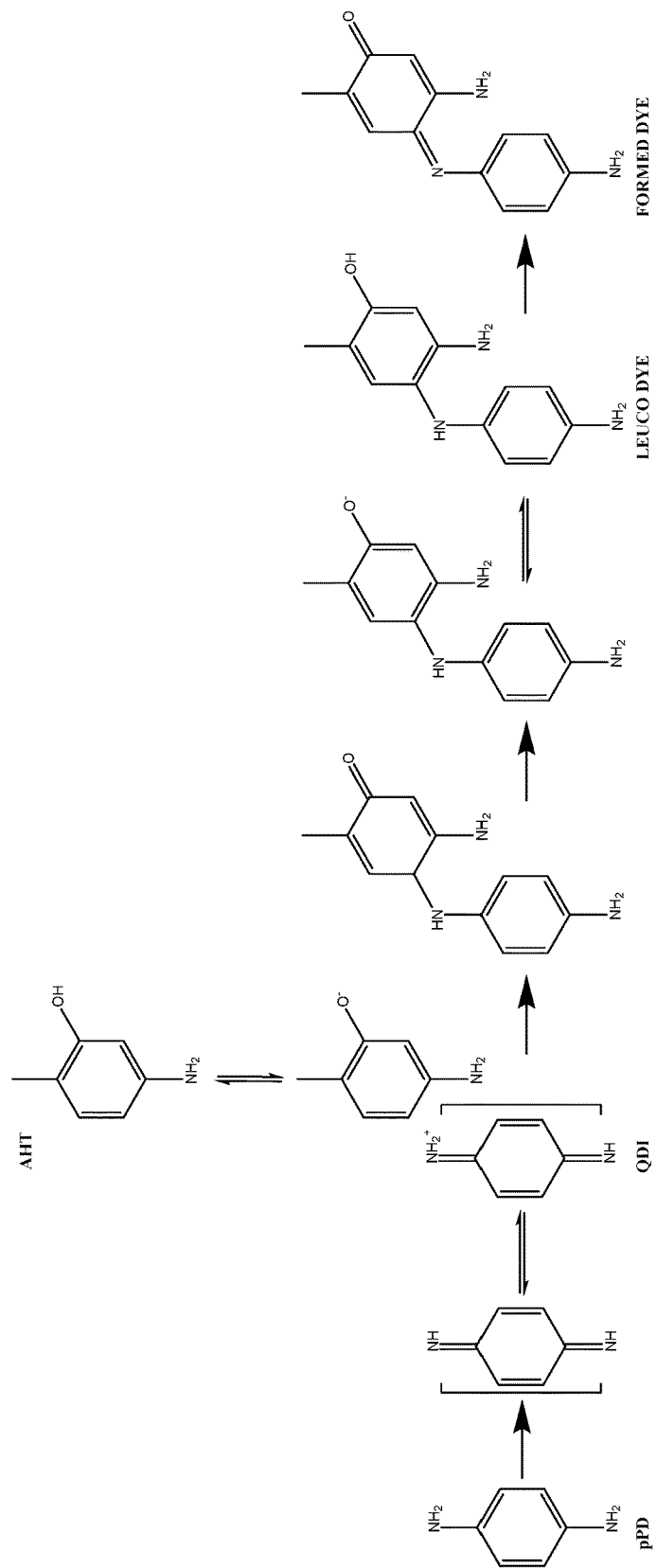
FIG. 4 illustrates an exemplary sequence of chemical reactions that can occur when treating hair with oxidative hair dyes.

For the formation of a dye within the hair a multistep process occurs. In the example illustrated in FIG. 4, a primary para-phenylenediamine (pPD) and a coupler amino hydroxytoluene (AHT) are considered. The pPD needs to be oxidized to the quinonediimine (QDI), referred to as the active intermediate. The AHT exists at least partially in its deprotonated state, the amount dependent on the local pH of the system. The QDI and AHT react together to form the colorless Leuco dye, which when oxidized forms the final colored formed dye. (Corbett, J. F. *J Soc Cosmet Chem* 1984, 35, (6), 297-310. Corbett, J. F. *J Soc Cosmet Chem* 1969, 20, (4), 253-263) Whilst not wishing to be bound by theory, it is believed that the initial oxidation of the primary and the subsequent initial reaction with the coupler are the rate limiting steps. This may then reduce the complex scheme to the following key steps.

The initial oxidation of the primary to the active intermediate is given by:

$$[P] + [H_2O_2] \underset{k_{p2}}{\overset{k_{p1}}{\rightleftharpoons}} [P^*]$$

Here, $k_{p_1}$ is the forward rate constant and $k_{p_2}$ is the backward rate constant. The coupling of the active intermediate [P*] with the coupler [C] to give the formed dimer dye [PC] is given by $$[P^*] + [C] \xrightarrow{k_{pc_1}} [PC]$$

Here $k_{pc1}$ is the rate constant for the reaction of the active intermediate with the coupler.

The coupling of the active intermediate [P*] with formed dye [PC] to give a so called trimer [PCP] is given by $$[P^*] + [PC] \xrightarrow{k_{pc_2}} [PCP]$$

Here $k_{pc2}$ is the rate constant for the active intermediate with the initially formed dimer dye [PC]. The formation of trimers [PCP] is not possible with all couplers as some are classed as blocked couplers, and can only react with one primary dye.

These can then be collapsed into a series of differential equations to describe the relative concentrations over time of the different species, including the most important terms for the levels of formed dyes produced.

The change in the concentration of Primary P as a function of time can be expressed as follows $$\frac{d[P]}{dt} = -k_{p_1}[P]^a[H_2O_2]^b + k_{p_2}[P^*]^c$$

The change in the concentration of active intermediate P* as a function of time can be expressed as follows $$\frac{d[P^*]}{dt} = k_{p_1}[P]^a[H_2O_2]^b - k_{pc_1}[P^*]^d[C]^e - k_{pc_2}[P^*]^f[PC]^g$$

Here, the term [C] may be further corrected to account for the concentration of the coupler in the deprotonated form at the given reaction conditions.

The change in concentration of the coupler C can be given by $$\frac{d[C]}{dt} = -k_{pc_1}[P^*]^d[C]^e$$

The change in concentration of the formed dimer dye PC can be given by $$\frac{d[PC]}{dt} = k_{pc_1}[P^*]^d[C]^e - k_{pc_2}[P^*]^f[PC]^g$$

And finally, the change in concentration of the formed dye PCP can be given by $$\frac{d[PCP]}{dt} = k_{pc_2}[P^*]^f[PC]^g$$

The terms a through to g refer to the order of the species within the chemical reaction kinetics. These terms are for the simple situation of a single primary and coupler. Where more couplers are included a summation of terms is then required to account for the individual reaction pathways that can occur. For example, as mentioned above, the change in the concentration of a single active intermediate P* as a function of time, with a single coupler can be expressed as:

$$\frac{d[P^*]}{dt} = k_{p_1}[P]^a[H_2O_2]^b - k_{pc_1}[P^*]^d[C]^e - k_{pc_2}[P^*]^f[PC]^g$$

This can be expanded to include a series of couplers from 1 to n:

$$\frac{d[P^*]}{dt} = k_{p_1}[P]^a[H_2O_2]^b - \sum_{n=1}^{n=n} k_{pc_1}[P^*]^{d_n}[C_n]^{e_n} - \sum_{n=1}^{n=n} k_{pc_2}[P^*]^{f_n}[PC_n]^{g_n n}$$

Likewise as more primaries are included, additional expressions can be added to account for $P_m$ where m refers to the primary dye from 1 to m used in a given formulation.

When this series is described fully it cannot necessarily be uniquely solved. However, it can still be solved using computational techniques (or a solution approximated, computationally). This then provides, for a dye preparation with a given composition, a series of expected concentrations of the different colored species.

As mentioned already above, primary dyes are oxidized prior to reaction, and couplers react with the oxidized primaries. It is desirable to avoid the primaries reacting with themselves. In some cases, such reactions can form compounds which are not perceived as being safe for the user of the dye preparation. To discourage unwanted reactions of this kind, the level (molar concentration), of couplers is chosen such that there is always a sufficient amount of the coupler dyes to react with all of the primary dyes.

Different rules can be applied to ensure this. The following rule is one example. Here, all concentrations are molar levels.

Σ[Coupler]≥Σ[Primary]

This means that the total molar concentration of all couplers is greater than or equal to the total molar concentration of all primaries. For some dye compounds—for example, 1-Hydroxyethyl 4,5-Diamino Pyrazole Sulfate and 1-hexyl-1H-pyrazol-4,5 diamine sulfate (2:1)—it may be desirable to build in a larger margin to account for the rapid rate of reaction. For example, the left hand side may be set to be at least 1.05 times the right hand side. In some other examples, the rule that is used may take into account the ability of some couplers to react with multiple primaries.

Within these bounds, the relative proportions of the primaries and the relative proportions of the couplers, respectively, can be chosen independently—that is, the concentration of each primary can be selected independently of the other primaries, and the concentration of each coupler can be chosen independently of the other couplers.

In the present embodiment, the levels of the couplers are chosen freely. Then, using a rule such as the one above, the ratio of primary to coupler is calculated, which sets the total level of primary dye that is paired within the model.

The computational model can be used to predict the final concentrations that will be obtained, based on a series of discrete starting concentrations for the primary dyes—for example, using up to three different primary dyes. In the present embodiment, the series of molar percentage ratios for the individual primary dyes differ in steps of 5%. For example, in a system using two primary dyes, the relative concentrations can be varied from 100% of a first primary and 0% of a second primary, in 5% increments, to 100% of the second primary. This gives a series of 21 different possible ratios. For three primaries, the number of combinations is greater, because each of the three primary dyes can be considered at incremental concentrations. Higher order combinations of primary dyes may also be calculated, even though the graphical representation may be more complex.

The ratio of the primary dyes that is predicted to give the nearest match to the target shade is then fixed, and the shade can be further optimized thereafter by changing the relative concentrations of the couplers (within the constraints of the rule mentioned above).

Expressions can also be derived to account for the interaction of direct dyes with the hair. In this situation the case is simplified due to absence of chemical reactions, but still needs to account for the time dependent absorption of the dyes with the hair. A simple expression for this process is:

$$\frac{d[D_{ads}]}{dt} = k_1 SF(t)$$

where $k_1$ is the rate of direct dye adsorption and S refers to a term which defines the sticking probability of the direct dye when it interacts with the hair surface, and F(t) is the time dependant flux of the direct dye at the hair surface. More extensive expressions can be created to describe the adsorption of multiple direct dyes, which also takes into account the rates of desorption.

The computational component 420b which predicts the concentrations of chemical species (in particular, melanin) in the hair fibers will now be discussed.

Different individuals have different levels of melanin in their hair, and even different melanin types, both Eumelanin and Pheomelanin. Whilst not wishing to be bound to theory, it is believed that during bleaching both the conjugation of the melanins is decreased, leading to less absorbance (and therefore greater reflectance) of light, and that the scattering properties of the melanin may also be altered. This results in a lower concentration of the initial melanin species, and the potential formation of new, differently colored, melanin species. By one reaction pathway, the original melanin has its color removed. This will be denoted "de-colored" melanin. By a second reaction pathway, the original melanin is converted to a different color. Meanwhile, some of the melanin remains unchanged. While it is possible to describe these reactions in many ways, here one example is discussed but is considered to be non-limiting. The process of melanin bleaching can be described by the following differential equations:

$$\frac{d\,[Melanin]}{dt} = -k_2[Melanin]^a[H_2O_2]^b - k_2[Melanin]^c[H_2O_2]^d$$

$$\frac{d\,[Melanin\,(de\ color)]}{dt} = k_1[Melanin]^a[H_2O_2]^b$$

$$\frac{d\,[Melanin\,(different\ color)]}{dt} = k_2[Melanin]^c[H_2O_2]^d$$

Within the context of melanin bleaching $k_1$ is the rate of melanin decoloring, $k_2$ is the rate of changing melanin to a different color and the terms a through to d refer to the order of the species within the chemical reaction kinetics. With these expressions, and knowing the initial concentrations of melanins and hydrogen peroxide within the hair it is possible to predict the resulting amount of color after the treatment time due to the melanin. Those skilled in the art will understand that the situation is more complex due to the impact of the reaction conditions. For example, the temperature and pH are known to impact the kinetic terms of the bleaching reaction.

The computational component 430, which predicts the color resulting from the chemical species in their respective concentrations, will now be discussed.

To predict the apparent color of the hair after treatment, the amount of light reflected at wavelengths between 380 and 780 nm is needed. This is the visible range of light, and will be used to compute L*a*b color spaces via the tristimulus XYZ functions in combination with the spectral distribution of a given light source.

The approach for predicting the amount of light reflected, $R(\lambda)$, may take several expressions.

In a first example:

$$R(\lambda) = e^{-\beta(\lambda)}$$

Where $$\beta(\lambda) = L \sum_{p=1}^{p=m} \sum_{c=1}^{c=n} C_{pc}\varepsilon(\lambda)_{pc} + L \sum_{d=1}^{d=x} C_d \varepsilon(\lambda)_d + L \sum_{a=1}^{a=x} C_a \varepsilon(\lambda)_a$$

Here $\beta(\lambda)$ is the amount of absorbance given by L, the length of light passage through the hair sample. $C_{pc}$ is the molar concentration of a given formed Primary (from 1 to m)/Coupler (from 1 to n) combination within the length of the light passage through the hair, and $\varepsilon(\lambda)_{pc}$ is the molar extinction coefficient (L mol$^{-1}$ cm$^{-1}$) of a given formed Primary/Coupler combination. $C_d$ is the molar concentration of a given direct dye (from 1 to x) within the length of the light passage through the hair, and $\varepsilon(\lambda)_d$ is the molar extinction coefficient (L mol$^{-1}$ cm$^{-1}$) of a given direct dye. $C_a$ is the molar concentration of a given hair component, a, within the length of the light passage through the hair, and $\varepsilon(\lambda)_a$ is the molar extinction coefficient (L mol$^{-1}$ cm$^{-1}$) of the hair component, a. The hair components denoted by the subscript "a" can include melanin species, proteins, or other components. The molar extinction coefficient is a material property of each chemical species which determines how it absorbs light at each wavelength. The molar extinction coefficients are stored within the model for each of the chemical species to be considered.

A second example of an approach to predict the reflectance spectrum $R(\lambda)$, via Kubelka Munk theory, is:

$$R(\lambda) = 1 + \frac{K(\lambda)}{S(\lambda)} + \left[\left(\frac{K(\lambda)}{S(\lambda)}\right)^2 + 2\left(\frac{K(\lambda)}{S(\lambda)}\right)\right]^{\frac{1}{2}}$$

Where K/S is given by the following expression $$\frac{K(\lambda)}{S(\lambda)} = \frac{\sum_{Hair=1}^{Hair=a} C_{Hair}K(\lambda)_{Hair} + \sum_{Mel=1}^{Mel=b} C_{Mel}K(\lambda)_{Mel} + \sum_{p=1}^{p=m}\sum_{c=1}^{c=n} C_{PC}K(\lambda)_{PC} + \sum_{d=0}^{d=r} C_d K(\lambda)_d}{\sum_{Hair=1}^{Hair=a} C_{Hair}S(\lambda)_{Hair} + \sum_{Mel=1}^{Mel=b} C_{Mel}S(\lambda)_{Mel} + \sum_{p=1}^{p=m}\sum_{c=1}^{c=n} C_{PC}S(\lambda)_{PC} + \sum_{d=0}^{d=r} C_d S(\lambda)_d}$$

Where $K(\lambda)_x$ is the molar absorbance term of the absorbing species X, wherein X denotes terms for Hair, Melanin, Oxidative and Direct dye components, $S(\lambda)_x$ is the molar scattering term of the absorbing species X and $C_x$ is the molar concentration of the species X. "Mel" is short for "Melanin". Preferably each of the numerator and denominator includes at least two terms. In the example given above, each of the numerator and denominator includes four terms—a first summation describing one or more chemical components of the hair, a second summation describing one or more melanin species, a third summation describing one or more formed Primary/Coupler combinations, and a fourth summation describing the optional one or more direct dyes.

Other expressions for $R(\lambda)$ can also be considered. A third example is:

$$R(\lambda) = \frac{1 - R(\lambda)_g \left[\left(\frac{S(\lambda) + K(\lambda)}{S(\lambda)}\right) - \frac{\left(\left(\frac{S(\lambda)+K(\lambda)}{S(\lambda)}\right)^2 - 1\right)^{\frac{1}{2}} \coth\left(\left(\left(\frac{S(\lambda)+K(\lambda)}{S(\lambda)}\right)^2 - 1\right)^{\frac{1}{2}} SL\right)}{}\right]}{\left(\frac{S(\lambda)+K(\lambda)}{S(\lambda)}\right) - R(\lambda)_g + \left[\left(\frac{S(\lambda)+K(\lambda)}{S(\lambda)}\right) - \left(\left(\frac{S(\lambda)+K(\lambda)}{S(\lambda)}\right)^2 - 1\right)^{\frac{1}{2}} \coth\left(\left(\left(\frac{S(\lambda)+K(\lambda)}{S(\lambda)}\right)^2 - 1\right)^{\frac{1}{2}} SL\right)\right]}$$

Where S and K are the same as defined previously and L is the thickness of the hair sample.

The term $R(\lambda)$ may optionally be converted from a theoretical reflectance spectrum $R_{Theory}$, to a measured reflectance spectrum $R_{measured}$, using the Saunderson equation or other similar conversion to account for surface effects.

$$R(\lambda)_{measured} = \frac{R(\lambda)_{Theory}(1 - F(\lambda)_{ext} - F(\lambda)_{int} + F(\lambda)_{ext}F(\lambda)_{int} - \alpha(\lambda)F(\lambda)_{int})}{1 - F(\lambda)_{int}R(\lambda)_{Theory}}$$

Here $R_{theory}$ is the theoretical reflection value and $R_{measured}$ is the expected measured value after taking into account surface Fresnel reflectance effects due to refractive index differences between hair and air, and where a is the relative proportion of specular reflection which propagates into the spectrophotometer at each wavelength, and $F(\lambda)_{int}$ is the internal Fresnel reflectance between the hair and the boundary region of the hair and $F(\lambda)_{ext}$ is the external Fresnel reflectance from the outside of the hair When the $R(\lambda)$ has been computed for the given formulation, it is then possible to transpose this spectrum into an L*a*b representation of the color. The following approach is used.

$$L^* = 116 f\left(\frac{Y_S}{Y_W}\right) - 16$$

$$a^* = 500\left(f\left(\frac{X_S}{X_W}\right) - f\left(\frac{Y_S}{Y_W}\right)\right)$$

$$b^* = 200\left(f\left(\frac{X_S}{X_W}\right) - f\left(\frac{Z_S}{Z_W}\right)\right)$$

Where the following expressions are required for the f( ) terms, shown here for X, but equally applicable for Y and Z terms.

$$\text{If } f\left(\frac{X_S}{X_W}\right) > \left(\frac{6}{29}\right)^3 \quad f\left(\frac{X_S}{X_W}\right) = \left(\frac{X_S}{X_W}\right)^{\frac{1}{3}}$$

$$\text{If } f\left(\frac{X_S}{X_W}\right) \le \left(\frac{6}{29}\right)^3 \quad f\left(\frac{X_S}{X_W}\right) = \frac{1}{3}\left(\frac{29}{6}\right)^2 \left(\frac{X_S}{X_W}\right) + \frac{4}{29}$$

And where the tristimulus values are obtained via:

$$X_W = \sum_{\lambda=380}^{\lambda=780} I(\lambda)\overline{x}(\lambda)$$

$$Y_W = \sum_{\lambda=380}^{\lambda=780} I(\lambda)\overline{y}(\lambda)$$

$$Z_W = \sum_{\lambda=380}^{\lambda=780} I(\lambda)\overline{z}(\lambda)$$

Where I is the wavelength dependent spectral power density of a light source and $\overline{x}$, $\overline{y}$ and $\overline{z}$ are the selected CIE color matching function used within the given comparison.

And where $$X_S = \sum_{\lambda=380}^{\lambda=780} R(\lambda)I(\lambda)\overline{x}(\lambda)$$

$$Y_S = \sum_{\lambda=380}^{\lambda=780} R(\lambda)I(\lambda)\overline{y}(\lambda)$$

$$Z_S = \sum_{\lambda=380}^{\lambda=780} R(\lambda)I(\lambda)\overline{z}(\lambda)$$

Where $R(\lambda)$ is reported as a fraction of light reflected at a given wavelength.

When the resulting L*a*b* has been calculated, it may then if desired be transposed into further color coordinates, for example L*C*h* cylindrical polar coordinates by the following transformations.

$$C^* = \sqrt{(a^*)^2 + (b^*)^2}$$

$$h^* = \operatorname{atan}\left(\frac{(b^*)}{(a^*)}\right)$$

The resulting color predicted can now be expressed as either a reflectance curve, or as a three-dimensional color vector.

Suitable optimization strategies for calculating a composition based on a target shade will now be discussed.

Figure 3:
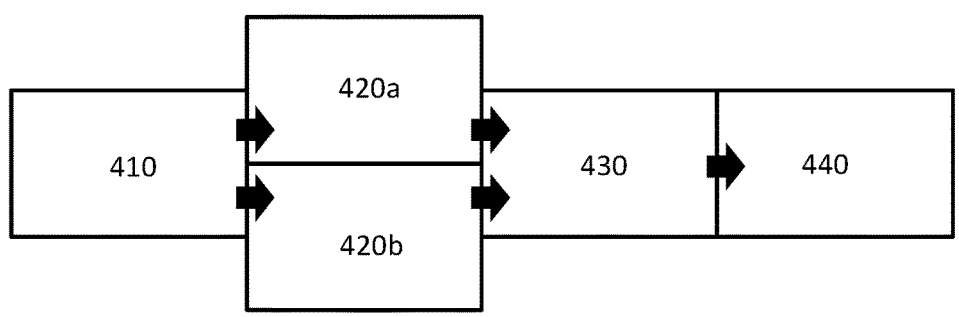
FIG. 3 illustrates a first computational model for use with the method of FIG. 1.

Within the computational model illustrated in FIG. 3, the calculations are performed from left to right—that is, starting with a composition and ending with a prediction of color. However what is important for the color formulator is the inverse—that is, to predict the composition that will deliver a given target color result.

In fact, for a given target shade, there may be a multitude of different routes to formulate the dyes to deliver the desired result. These may include different compositions that use the same dyes, or compositions which actually contain different dyes.

Figure 5:
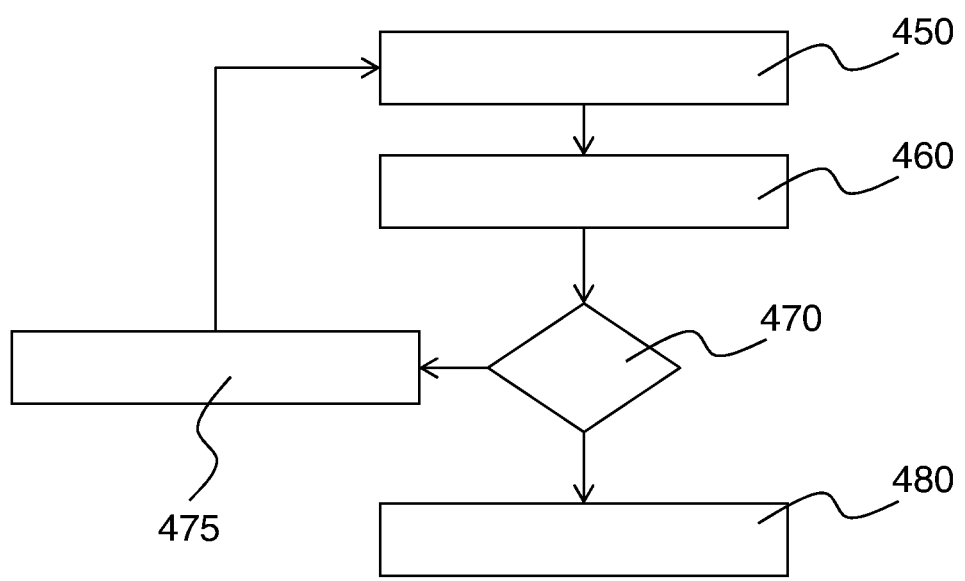
FIG. 5 illustrates an optimization scheme for calculating a composition using the computational model of FIG. 3.

What is therefore required is an optimization scheme to find good formulations to deliver the color target. This can be done as illustrated in FIG. 5. In step 450, the system starts with an initial composition. In step 460, the processor 120 uses the first computational model to predict the color that would be produced in the hair fibers, if they were treated with a preparation having the initial composition. In step 470, the processor compares this predicted color with the target shade. If the prediction does not match the target closely enough, the method proceeds to step 475; the composition is modified; and the sequence of steps repeats, starting with step 450. When (in step 470) the prediction from step 460 matches the target shade sufficiently closely, the method proceeds to step 480, outputting the current composition as a solution.

It may be preferable for the user of the tool to be able to provide at least one set of boundary conditions to the initial composition chosen. For example, the user may input a set of dyes that they would prefer to use, or may input an indication of the maximum level of each dye that they would like to consider. Candidate compositions that do not meet these requirements can be ignored, when searching for solutions.

In step 470, the processor can compare the predicted color and the target color in a variety of different ways, to decide if they are sufficiently well matched. For example, the absolute color values of the three dimensional L*a*b* color vectors may be compared using the following expression.

$$dE_{76} = ((L_{target} - L_{simulate})^2 + (a_{target} - a_{simulated})^2 + (b_{target} - b_{simulate})^2)^{1/2}$$

Here, the target and simulated values for L*a*b* are compared directly. The expression provides one way to determine a distance, based on color difference.

Alternatively more complex forms of distance based on color difference may be used for the comparison. For example, the CIEDE2000 color-difference formula, $dE_{2000}$ can be used. Further details of this formula may be found in Sharma, Wu, and Dalal, "The CIEDE2000 Color-Difference Formula: Implementation Notes, Supplementary Test Data, and Mathematical Observations", COLOR research and application, Volume 30, Number 1, February 2005.

Distance measures of the types mentioned above may be appropriate, for example, if the target shade has been specified as a color vector, as is the case in the present embodiment.

In other embodiments, the target shade may be specified by a reflectance function. In this case, the reflectance spectrum of an existing sample can be measured directly, to derive the target specification. In step 470, the full spectral reflectance curve of the target shade and a predicted spectral reflectance curve simulated in step 460 can be compared. For example, the two spectra can be compared by using the following expression:

$$\Delta = \sum_{\lambda=380}^{\lambda=780} \operatorname{ABS}(R_{target}(\lambda) - R_{simulated}(\lambda))$$

Where ABS is a function that returns the absolute value or modulus of the difference, and is always either zero or a positive value for the difference between the two reflectance values at a given wavelength. An alternative expression is:

$$\Delta = \left( \sum_{\lambda=380}^{\lambda=780} \frac{(R_{target}(\lambda) - R_{simulated}(\lambda)^2}{n} \right)^{\frac{1}{2}}$$

Where n is the number of different wavelengths which are present within the summation. If desired, an additional weighting may be applied to the wavelengths to account for their relative importance for visual perception. This can be based upon the $\bar{x}$, $\bar{y}$ and $\bar{z}$ terms referred to earlier.

In step 470, a composition will be accepted or rejected, based on the outcome of the comparison. Whether to accept or reject the composition can be decided by comparing the distance measure (such as one of those defined above) with a predetermined threshold. When a composition fails (that is, the distance from the target is greater than the threshold), a solving approach is needed to suggest one or more modified compositions, in step 475, for the next iteration. This can be done using so called gradient optimization methods, or through other probabilistic mathematical techniques.

It may be preferable to have an approach which is specifically designed to produce a plurality of different composition options for achieving the target shade, for example through the use of evolutionary or genetic algorithms.

It may be preferable to perform multi factor optimization, wherein a second criterion, other than color, is considered when producing a solution, or a series of solutions. Examples of such additional criteria include but are not limited to dye solubility, expected rheology or manufacturing cost. Other examples include a toxicological profile of ingredients within the preparation; a permanence of the result of treatment by the preparation, in particular a resistance to degradation due to at least one of: light at visible wavelengths, ultra-violet light, sweat, and water; an ionic strength of the preparation; a stability of the preparation; a coverage of the preparation on grey hair; an extent to which the preparation will stain the skin during treatment; an ability of the preparation to deliver uniform color from a root to a tip of hair fibers; an ability to tailor the penetration depth of the color delivered by the preparation; and a shine of the hair fibers after application of the preparation.

In step 320 of the method illustrated in FIG. 1, there are a variety of ways in which the system can modify the first image. One particularly advantageous way is based on the method proposed in EP 14189661.3. This will now be summarized below. Further details, where necessary, can be found in the above-referenced patent application.

Figure 6:
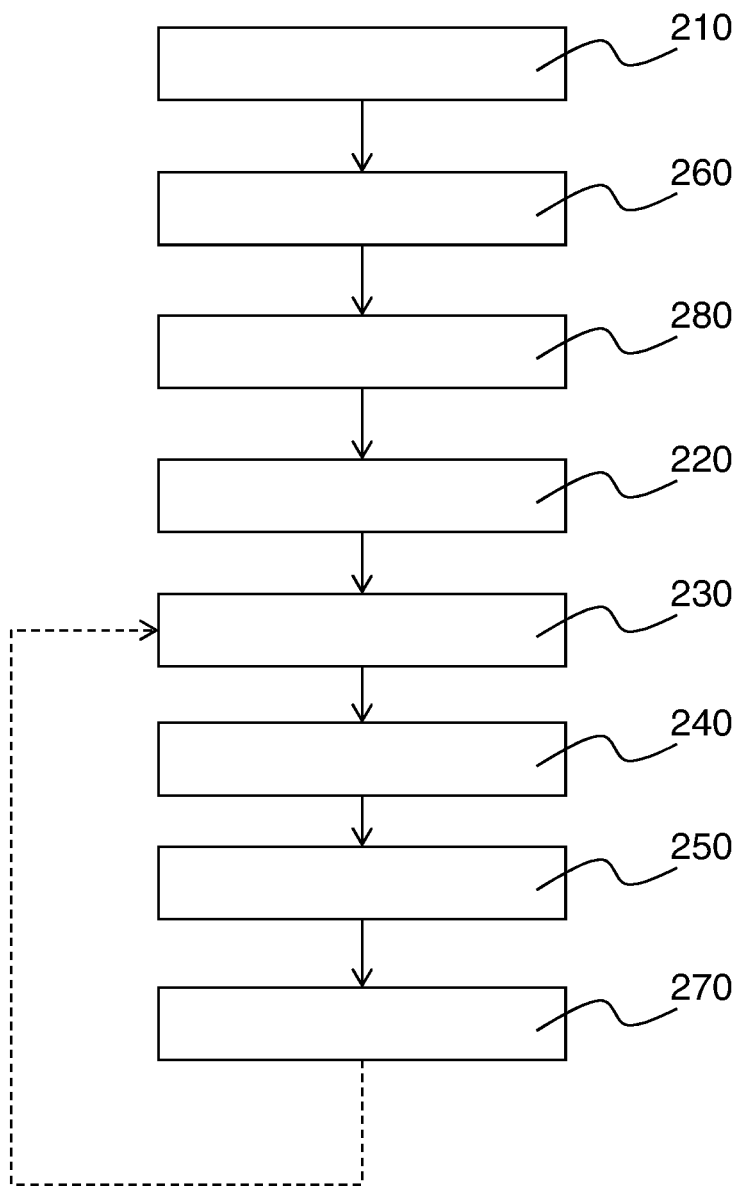
FIG. 6 is a flowchart illustrating a method of synthesizing an image of fibers, for use in the method of FIG. 1.

FIG. 6 is a flow-chart illustrating the method. In this example, the first image, which forms the starting point for the modification, is a synthetic image, generated using computer graphics techniques. Nevertheless, this synthetic image preferably represents the appearance of the real hair fibers that are intended to be treated with the hair dye preparation. In other words, the synthetic first image is a virtual rendering of the real hair fibers. Modifying the first image will comprise rendering a modified synthetic image. As mentioned previously above, using synthetic images to define the target shade has the advantage that illumination and other factors can be controlled in the synthetic image.

The real hair fibers to be treated may themselves already have been treated in some way, previously. For example, they may already have been pre-colored to create a closer approximation of the target shade. In this way, the first image may represent untreated ("virgin") hair fibers, or may represent hair fibers that have already been treated to some extent.

In greater detail, referring to FIG. 6: a second computational model describing the interaction of light with fibers is provided (step 210). This model may be stored in the memory 110 and provided to the processor 120 during an initialization phase of the method. In step 220, the processor 120 obtains a first set of hair fiber parameters for use with the model. The first set of fiber parameters describes the hair fibers 160 to be treated. A way of obtaining the fiber parameters will be described in greater detail below. In step 230, the processor 120 modifies the first set of fiber parameters to produce a second set of hair fiber parameters. The second set of fiber parameters describes a modified version of the real hair fibers 160. In this example, the first set of parameters includes at least one parameter relating to a color of the hair fibers 160. This is modified in the second set of parameters, such that the second set of parameters describes a modified version of the hair fibers 160 having a different color. This models the effect of dyeing the hair fibers 160. The parameters are modified in response to user input. In one example, the system provides the user with a user interface to modify the parameters and the user inputs modified parameters using this interface. In step 240, the processor 120 simulates how light would interact with the modified fibers. This comprises calculations using the second computational model together with the second set of hair fiber parameters. Based on the result of the simulation 240, the processor 120 renders a synthetic image showing the appearance of the modified fibers (step 250). This is the "modified image" which is the output of step 320 in FIG. 1. The processor 120 may store the synthetic image in the memory 110. In step 270, it displays the synthetic image on the display screen 140.

The user can then inspect the displayed synthetic image. If the user is satisfied with the appearance of the modified fibers in the image, then this image can be used to derive the target specification for calculating the dye composition (step 330).

In this example, the user may be a hair-care professional. The real hair fibers 160 (which are described by the first set of fiber parameters) may be a standard sample (tress) of hair. The hair care professional uses the (synthetic) modified image as a way to define the hair color that the professional wishes to achieve for this tress.

Optionally, other parameters may be used with the second computational model to generate the synthetic image, in addition to the second set of hair fiber parameters. Preferably, the processor 120 obtains light source parameters for use with the second computational model, in step 260. The light source parameters describe a light source, which is used to illuminate the modified fibers in the virtual world of the simulation. Preferably, the light source parameters comprise an omnidirectional image of a real scene, also known as a light probe image. Preferably, the processor 120 also obtains head parameters for use with the model, in step 280. The head parameters describe the positions of a plurality of hair fibers on a head, defining a hair style. In the example of FIG. 6, the position, orientation, length, and shape of each individual hair on the (virtual) head is defined by the head parameters. The optical characteristics of the hair fibers are described by the fiber parameters and the light illuminating the fibers on the head is determined from the light source parameters. The second computational model defines how all of these parameters are combined, to simulate the interaction of the light with the fibers and render a resultant synthetic image. Thus, the computational model captures the most important physical characteristics that affect the appearance of hair fibers in the real world. The fiber parameters, light source parameters, and head parameters define a numerical representation, in a virtual world, for simulating the same physical processes that occur in the real world to form a real image of a head of hair.

Optionally, after the synthetic image is displayed in step 270, the user may decide that he/she is not yet satisfied with the appearance of the modified hair fibers. In this case, the user may provide further user input to the processor 120, in response to which the processor further modifies the hair fiber parameters. Essentially, as shown by the dashed line in FIG. 6, the method proceeds to step 230 again and the steps of simulating 240 and rendering 250 a synthetic image are performed again. The method can proceed in an iterative fashion, in this way—successively refining the fiber parameters, until the user is satisfied with the appearance of the modified fibers in the synthetic image. Once the user is satisfied, the synthetic modified image will be used to derive a target specification, in step 330.

Although not mentioned explicitly above, the synthetic first image can be obtained in step 310 by simulating and rendering using the second computational model with the first set of hair fiber parameters. In other words, both the first image and the modified image can be rendered by using the same computer graphics techniques.

In step 220, described above, it is necessary to obtain the first set of hair fiber parameters. In this example, these describe the real hair sample 160.

Figure 7:
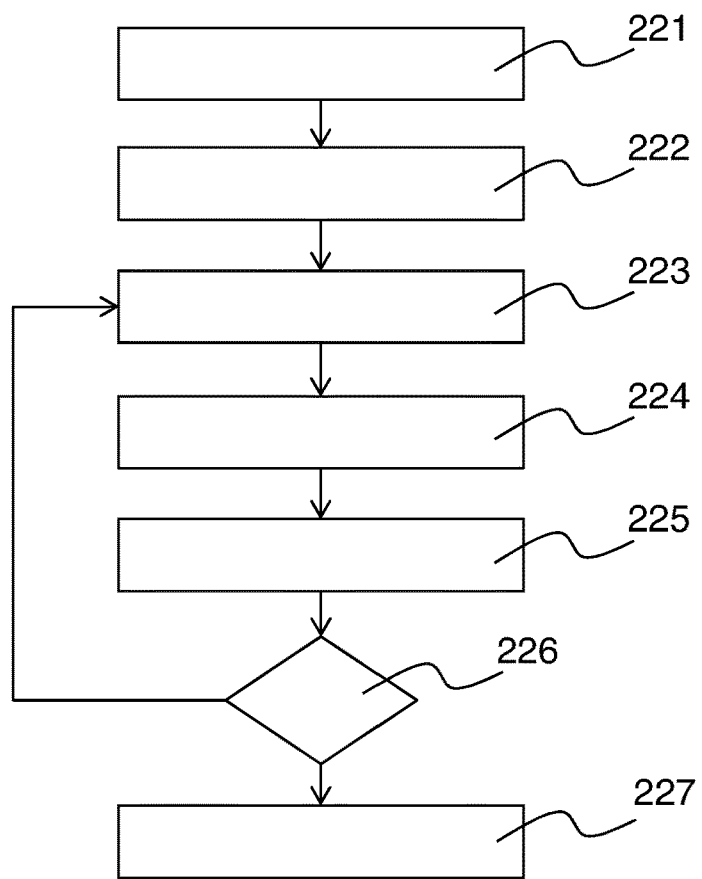
FIG. 7 is a flow-chart illustrating a method of measuring the optical properties of hair fibers.

FIG. 7 is a flow-chart illustrating a method for measuring the optical properties of fibers, which allows the first set of hair fiber parameters to be obtained. Further details of this method are found in EP 14189661.3. In step 221, the camera 150 captures an image of the hair fibers 160. In step 222, the processor 120 processes the image to determine an initial set of estimated fiber parameters. The method then follows an "analysis by synthesis" approach. In step 223, the processor 120 simulates, using the computational model and the initial estimated fiber parameters, how light would interact with a plurality of fibers having those initial estimated parameters. In step 224, the results of this simulation are compared with the image captured by the camera 150. An error metric is computed, characterizing the difference between the simulated results and the real image. In step 225, the processor 120 updates the estimated fiber parameters, based on the error metric. The processor then tests, in step 226, whether the estimated fiber parameters have converged to stable values yet. If the estimated fiber parameters have not yet converged sufficiently, the steps of simulating 223, computing the error metric 224, and updating the parameters 225 are repeated. The iterations continue until the estimated fiber parameters converge—that is, until the previous set of parameters and the updated parameters after step 225 are sufficiently similar. Convergence can also be determined by detecting when the magnitude of the error metric falls below a predefined threshold. When the parameters have converged, the method proceeds to step 227 and the first set of fiber parameters, describing the hair fiber sample 160, are determined by setting them equal to the converged estimated fiber parameters.

In this example, each of the first and second sets of hair fiber optical parameters comprises parameters for describing: (i) how incident light is reflected from a first surface of a hair fiber; (ii) how incident light is transmitted through the first surface of the hair fiber and a second surface of the hair fiber; (iii) how incident light is transmitted through the first surface of the hair fiber, reflected from the second surface of the hair fiber, and transmitted through a third surface of the hair fiber; as well as (iv) how incident light is absorbed by the hair fiber. Further details of suitable hair fiber optical parameters are found in EP 14189661.3.

One way of deriving a target specification from the modified image in step 330 will now be described. This can be used with synthetic images generated by the method of FIG. 6, or any other kind of modified image. Assuming that the modified image is stored in an RGB format, each pixel in the bitmap image is converted firstly to XYZ coordinates, and then from XYZ to L*a*b*. The conversion from RGB to XYZ will be well known to those skilled in the art. The conversion from XYZ to L*a*b* has been discussed previously above. The average value of the L*a*b* color vector for all pixels in the image is then used as the target specification.

In the above example, it is assumed that the modified image is a "close up" showing only a tress of hair. If the modified image shows other features, such as skin or background, then the image should be cropped to a version that includes only hair, or the non-hair pixels in the image should be ignored in some other way (for example by marking hair and non-hair and calculating the average only over the hair pixels).

The foregoing description has explained one embodiment according to the first aspect of the invention. Various optional refinements are possible and some of these will now be described.

A first optional variation relates to step 320 in FIG. 1.

As discussed above, it is possible to use synthetic images to assist the user in defining the target shade. The user can modify the synthetic image until the hair shown in this image has the desired color. However, a synthetic image that the user interacts with to define the target shade might not have optimal properties for deriving the target specification. For example, it might be more informative, for the user, to interact with a synthetic image that shows a head of hair in a particular hair style, with a particular background, or under particular illumination. It may be difficult to derive an objective target specification from such a synthetic image in such a way that the target specification is independent of these factors.

For this reason, once the user has found the desired color, it may be appropriate to render an additional synthetic image, for deriving the target specification. This additional synthetic image shows hair with the same hair fiber parameters chosen by the user, but rendered in a standard scene, with standard illumination. By way of example, the standard scene could show a close up of a tress in a "bob" hairstyle. The illumination is preferably spatially homogenous and is preferably made up of white light having a uniform spectrum—that is, substantially constant amplitude across all wavelengths. This standard scene can allow the target specification to be derived consistently and objectively—for example, in the form of an average L*a*b* value, as described above. The target specification is based on the additional synthetic image; therefore, it is based on the modification that was performed to the first image. This modification is captured by the second set of hair fiber parameters, which are used to render the additional synthetic image. Looked at another way, this can be understood as the additional synthetic image becoming the "modified image" for the subsequent step 330 of deriving the target specification.

A second optional variation relates to step 330 in FIG. 1.

Figure 8:
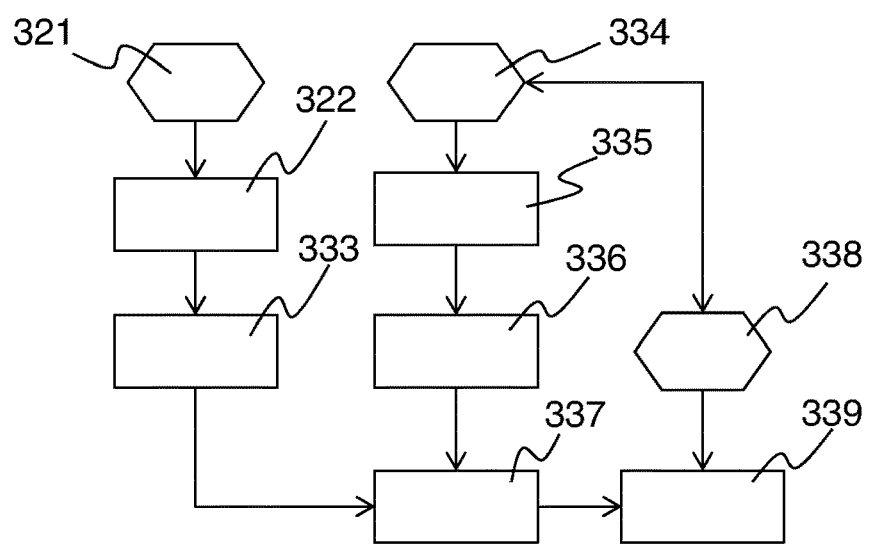
FIG. 8 is an information flow diagram, illustrating an alternative method of deriving a target specification, for the method of FIG. 1.

When a synthetic image is used to derive the target specification, it may be desirable to derive the target specification in a slightly more complicated way than the examples suggested previously above. This is based on the recognition that an L*a*b* value derived directly from a synthetic image might not be as accurate as one measured in the real world. One approach that can address this is illustrated in FIG. 8.

The computer 130 stores a database of hair fiber optical parameters in its memory 110. Each of these sets of parameters describes a sample (for example, a tress) of real hair fibers of a different shade. These samples may be representative of the range of hair colors that has been achieved with an existing palette of hair dyes. Preferably, each set of hair fiber optical parameters is obtained by analyzing the respective sample (for example, using a method like that illustrated in FIG. 5). Also, for each sample, an L*a*b* color vector is measured directly using a spectrophotometer. These measured color vectors are also stored in the database, in memory 110, associated with the respective hair fiber optical parameters.

One of the products of step 320 is the second set of hair fiber parameters. This second set of hair fiber parameters is denoted 321 in FIG. 8. The processor 120 compares the second set 321 of hair fiber parameters with the sets of hair fiber parameters stored in the database and identifies the most similar set in the database. The fiber parameters can be compared using a distance metric such as Euclidean distance, or a more complex metric such as the $dE_{2000}$ measure defined previously above. The most similar set of hair fiber parameters in the database is denoted as the nearest neighbour set 334. The associated measured L*a*b* color vector in the database is denoted the nearest neighbour measured color vector 338. The corresponding hair fibers are called the nearest neighbour hair fibers.

In step 335, the processor 120 simulates, using the second computational model and the nearest-neighbour set 334 of hair fiber optical parameters, how light would interact with the nearest neighbour hair fibers; and renders, based on the result of the simulation, a nearest neighbour synthetic image. This is a synthetic image showing the appearance of the nearest neighbour hair fibers. It is preferably rendered under the standard scene conditions discussed above in connection with the first optional variation.

In step 336, the processor 120 derives a nearest neighbour synthetic color vector from the nearest neighbour synthetic image. This can be done by converting the RGB image to XYZ and then L*a*b* and calculating an average L*a*b*color vector in the manner described previously above. The nearest neighbour synthetic color vector is affected by the virtual illumination used in the simulation and rendering step 335. The nearest neighbour measured color vector 338 is measured in the spectrophotometer using light from a real light source. To the extent that the real illumination from the real light source and the virtual illumination are different, the nearest neighbour synthetic color vector may differ from the nearest neighbour measured color vector.

Preferably, in step 322, the processor implements the first optional variation described above, in which it simulates and renders an additional synthetic image using the second set 321 of hair fiber parameters. This additional synthetic image forms the modified image for step 333. In step 333, the processor derives 333 a modified image color vector from this modified image. This L*a*b* color vector is derived in the same way discussed above, by converting from RGB, to XYZ, to L*a*b* and taking an average L*a*b* color vector.

In step 337, the processor 120 calculates 337 a color difference between the nearest neighbour synthetic color vector from step 336 and the modified image color vector from step 333. This color difference quantifies the difference—determined under virtual illumination—between the appearance desired by the user and the most similar real dyed sample recorded in the database.

In step 339, the processor adds the ("virtual") color difference from step 337 to the ("real") measured color vector 338. The result of this calculation provides the target specification for the step 350 of calculating the composition. In other words, the target specification is constructed from a real, measured L*a*b* value (of the nearest neighbour hair sample) together with a color difference determined from synthetic images. It has been found that, although absolute color vectors derived from synthetic images may contain inaccuracies due to the limitations of the second computational model, color differences determined from such images can be more reliable. The method of FIG. 8 allows the target specification to be based on a color difference determined synthetically, and an absolute color vector determined by real measurement.

It is believed that this approach can help to correct for imperfect mapping of the color space and sub-optimal specification of the (virtual) illumination used in the synthetic image.

Figure 9:
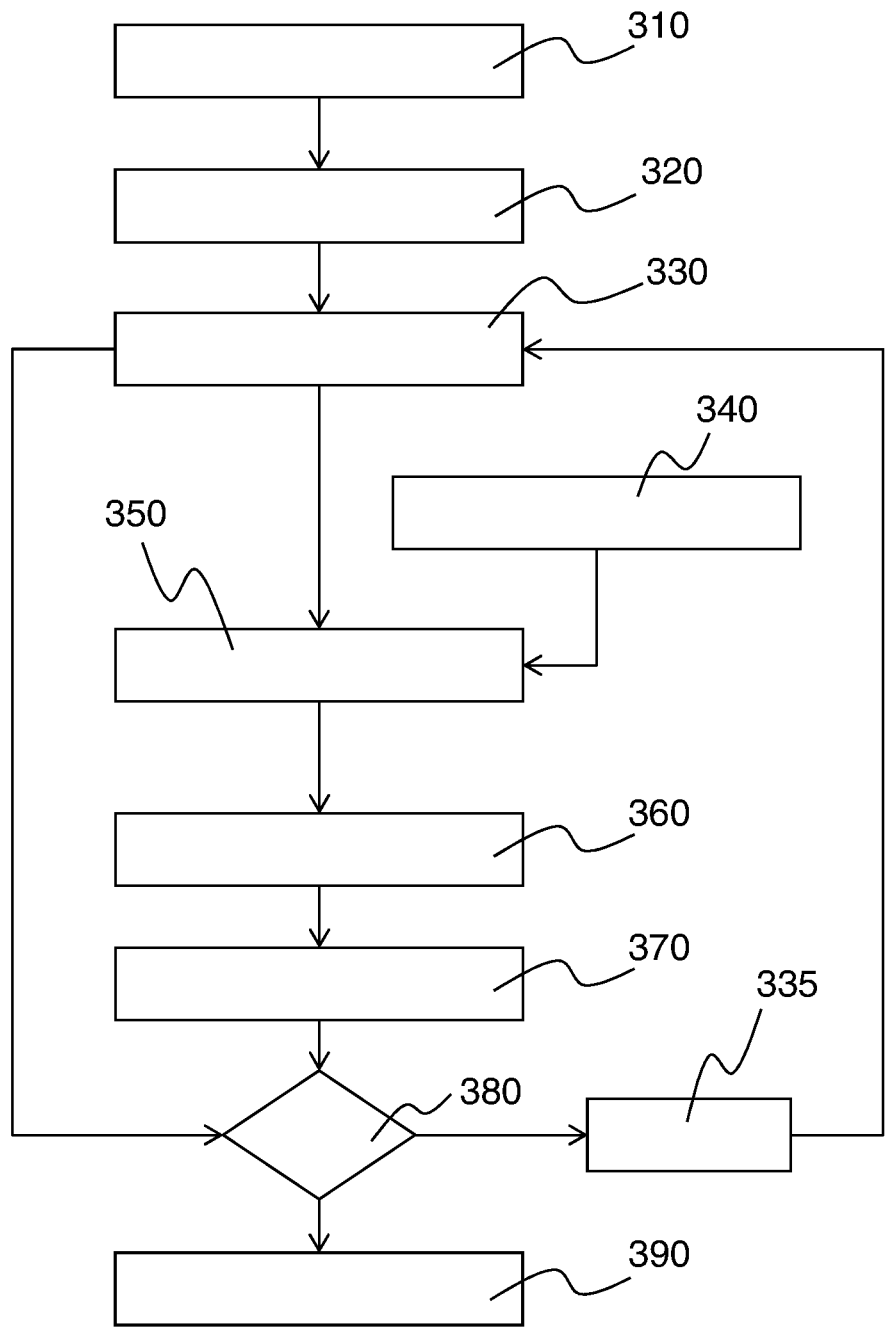
FIG. 9 is a flowchart illustrating an iterative method based on the method of FIG. 1.

In general, the first computational model may not be accurate enough to allow the composition of the hair dye preparation to be calculated perfectly at the first attempt. To take account of this, a process of iterative refinement is proposed. This is illustrated in FIG. 9. The core method is similar to that of FIG. 1 and similar steps are labeled with the same reference numerals. The following discussion will focus on the additional steps performed according to the method in FIG. 9. After the composition of the preparation is calculated (for the first time) using the first computational model, in step 350, the preparation is actually made (step 360) and used to treat a hair sample (step 370). If the first computational model had perfectly modeled the dyeing process, then the treated hair sample would now exhibit the desired appearance. However, this is unlikely to be the case, in practice. In step 380, the treated hair fibers are compared with the desired appearance. Assuming that they do not match the desired appearance closely enough, the target specification is modified, in step 335, based on the result of the comparison. This updated target specification is then fed back into the method for the next iteration. In the next iteration, the processor 120 calculates 350, using the first computational model and the updated target specification, an updated composition for the preparation.

As the iterations proceed, the appearance of the treated hair fiber samples should approach the desired appearance more closely. Eventually, when the comparison in step 380 determines that they match closely enough, the method proceeds to step 390 and the composition determined in the last iteration of step 350 becomes the final composition of the hair dye preparation.

The step 380 of comparing the treated hair fibers with the desired appearance can be implemented in a variety of ways In some embodiments, the step of comparing comprises measuring a color difference between the target specification and the treated hair fibers; and modifying the target specification based on the measured color difference. When the target specification comprises a color vector in a 3-D color space, as discussed previously above, it can be convenient to measure the color difference in the same 3-D color space. For example, the color difference may comprise a color difference in L*a*b* color space.

The step 380 of comparing may comprise firstly measuring a representative color vector for the treated hair fibers.

This may involve capturing an image of the treated hair sample, followed by processing the image to extract the representative 3-D color vector. This can be done in the same manner described previously above—converting from an RGB captured image, to XYZ, and from XYZ to L*a*b*.

It is also possible to measure a representative color vector in other ways, without necessarily capturing an image of the treated hair sample. For example, a reflectance spectrum of the treated hair fibers may be measured using a spectrophotometer and the representative color vector may be derived from the measured reflectance spectrum.

In some other embodiments, a representative color vector can be obtained from "virtual" hair fibers in a synthetic image. To do this, the hair fiber optical parameters of the treated sample of hair fibers are obtained—for example, using a method like that illustrated in FIG. 5 and described previously above. The processor 120 then simulates and renders a synthetic image using these parameters. This synthetic image can then be processed to extract a representative color vector, in the same way as a real image. An advantage of extracting the representative color vector from a synthetic image, rather than from a real, captured image of the treated hair fibers is that the synthetic image can be rendered under a standard, controlled (virtual) illuminant. This can help to avoid bias in the color vector due to real illumination. It may be easier to control the "virtual" illumination in the second computational model than it is to control the illumination of the real treated sample of hair fibers.

Once a representative color vector has been obtained, the step of measuring the color difference may then comprise subtracting the representative color vector for the treated hair fibers from the target color vector (or vice versa). The color difference may be reduced to a single value using distance metric such as $dE_{76}$ or $dE_{2000}$, defined previously above. This can be compared with a predetermined threshold, in step 380, to decide whether the colors match closely enough.

The step 335 of modifying the target specification can also be implemented in a variety of ways.

In some embodiments, a color difference calculated in step 380 may be added to (or subtracted from, as appropriate) the previous target color vector, to produce the modified target color vector. The modified composition will then be calculated (in the next iteration) based on this modified target, using the first computational model in the same way as in the initial iteration. In this subsequent iteration, when a sample of hair fibers is treated with a preparation having the modified composition, it is hoped that the treated fibers should more closely match the target color vector. In other words, the color difference is preferably reduced, over the iterations. In this way, the process can iteratively converge on a modified composition which best matches the target color vector.

Optionally, the iterations can terminate when the measure of color difference ceases to decrease between iterations.

In some alternative embodiments, iterative refinement may be performed manually, rather than automatically as described above. After treating the hair fibers with the preparation, the treated hair fibers may be inspected visually (by a human operator) and compared with the target specification. If the treated fibers do not match the target specification closely enough, the operator may then manually adjust the calculated composition, to improve the color match between what is desired and what is actually achieved by using the preparation. This allows a human operator to refine the initial composition that was calculated automatically. This can account for inaccuracies or simplifications in the computational model (or models) that prevent a "perfect" result being achieved automatically. It might also be used to account for subjective or perceived differences between the desired appearance and the target specification.

In some other embodiments, the iterations may be semi-automatic. For example, a human operator may visually inspect the treated hair fibers and compare them with the target. Then, using his/her skill and experience, the operator can manually adjust the target specification to be used in the next iteration by the first computational model. This can allow automatic calculation of the composition, guided by manual intervention.

In one preferred embodiment, the step 380 of comparing the treated hair fibers with the desired appearance is performed automatically by the processor 120, but the calculation is based on prior measurements of human perception of color differences. This approach will now be described in greater detail.

The following approach can be used to determine if the treated hair fibers match a target specification and associated desired appearance. This can increase the precision compared with color acceptability assessments by human assessors. It has been found that it is difficult for a human assessor to decide if two hair colors are identical, due to an unintentional human bias in favor of detecting differences between the colors (even if there is no difference, or no perceptible difference). When human assessors are asked if two samples are different, they tend to see them as different, even if they are actually the same. However, by conducting a test with a panel of assessors, in which the assessors are shown pairs of samples whose colors have been precisely and objectively controlled, it is possible to determine a threshold color difference at which there is a significant change in the ability of the panel to consistently observe a significant difference between colors, versus the random noise detected when the panel are presented with images which are identical. In other words, below the threshold, the response of the panel to see a color difference is the same as when two identical colors are shown and above the threshold there is significant increase in the consistency of the panel to rate the images as different versus when two identical colors are shown.

This threshold is defined as the "detection threshold". Whilst not wishing to be bound by theory, this is believed to be a visual detection limit, which is broadly the same for all visual assessors who have full color perception. Although individual assessors may believe that they see a difference, for color differences below this detection threshold, in fact there is no perceptible difference. The detection threshold is found to change in different regions of color space. These detection thresholds are used to set limits for numerically measured color differences, to allow the processor 120 to automatically measure whether treated hair fibers meet the specified color target.

Although they have been described separately, for clarity, the iterative method of FIG. 9 can be combined with the "differential" method of FIG. 8, if it is desired.

In the embodiments described above, the target specification was derived based on modifying an initial image (the "first image") in some way. According to a second aspect of the invention, the target specification may be derived in other ways. In particular, it is not essential that the target specification is derived based on a modified image. Thus, a method according to an embodiment of the second aspect of the invention could be similar to the method illustrated in FIG. 1, but would omit the step 320 of creating a modified image. The target specification may be based directly on an image of real hair fibers. For example, it could be derived from the image in a similar manner to that described previously above—converting an RGB image to XYZ, and from there to L*a*b*, followed by calculating an average L*a*b* value. Alternatively, an L*a*b* value can be measured using a spectrophotometer, without the need to capture any image (that is, omitting step 310 as well as step 320).

A method such as this can be used to calculate a composition for a hair dye preparation that will replicate the color produced by another, pre-existing hair dye preparation. This may be useful when a dye needs to be reformulated for cost, safety, or other reasons.

When formulating a new hair dye preparation to match the treatment results of a pre-existing ("old") hair dye preparation, the following approach may be used experimentally in step 380.

The old hair dye preparation and new hair dye preparation to be tested are applied to a plurality of different hair types that represent different starting hair colors and optionally different levels of hair damage. The products are applied using an application protocol which is determined to be most relevant for the intended product usage conditions. By way of example, each of the two hair dye preparations may be applied to 3 to 10 different hair types, some of which are "virgin" uncolored hair, and optionally some which have been pre-damaged to represent "tip" hair.

The resulting color is measured using a spectrophotometer and converted into L*a*b coordinates, for each hair type and for both the old and new dye.

Alternatively, the L*a*b* coordinates can be obtained from synthetic images, by measuring the optical parameters of the hair samples, using a method as described above, and then rendering a synthetic image from each set of optical parameters. L*a*b* coordinates can be derived from each image in the same manner described previously above.

The L*a*b* color results obtained for the old and new hair dye preparations are compared using a mathematical function taking into account the results across all hair types to predict a form of average color difference across the different hair types studied. This can comprise calculating $dE_{76}=((L_1-L_2)^2+(a_1-a_2)^2+(b_1-b_2)^2)^{0.5}$ for each pair of samples. More preferably, the $dE_{2000}$ distance measure is used.

The difference in color is then compared to the appropriate detection threshold for the type of color tested. The detection thresholds are derived as discussed above. If the color difference is below the detection threshold, then the color result can be considered the same and no further work is needed to formulate the shade. If the color difference is higher than the detection threshold, then a further iteration is needed.

The embodiments above have been disclosed in the context of the apparatus shown in FIG. 2. This is just one exemplary implementation of the method in hardware. It may be suitable for applications both in salons and in development laboratories.

In a salon, the camera 150 may take a photo of the customer's hair 160. The customer (either by themselves or in consultation with a stylist or colorist) may provide user input to the computer 130 to indicate the desired appearance of the hair. And the calculation of the dye composition may be performed by the same computer 130. The dye preparation having the calculated composition may then be made in the salon—either manually by the colorist or automatically by a dispensing and mixing machine.

In a development laboratory, the hardware may be used in a similar way, but instead of a stylist, colorist, or salon customer, the operator may be a hair dye formulation expert.

For other applications, methods according to embodiments can be implemented differently in hardware, as appropriate. For example, it is possible to envisage a service providing mail-order customized dye preparations. To support such a business model, the hair dye preparation manufacturer may make available an app for a smartphone (or other personal portable electronic device). The smartphone app may implement a method according to an embodiment. Optionally, the smartphone app may implement the method with the assistance of a remote server. For example, the smartphone app may allow a user to capture an image of their hair using a camera in the smartphone. That is, the camera 150 may be replaced by a smartphone camera. The app may then allow the user to modify the image of their hair, to manipulate the shade. Simple modifications may be performed by a processor in the smartphone. More complex modifications, such as rendering synthetic images as described above with reference to FIG. 6, may be performed by a processor in a remote server. The processor in the server may be more powerful (in terms of calculation capabilities) than a typical smartphone processor. The calculations necessary to render a synthetic image of sufficient quality may be impossible (or too slow) on a smartphone processor. Similarly, the calculation of the dye composition in step 350 is likely to be implemented using a remote server, because of the heavy computational burden that may be involved.

In one example, the step 310 of obtaining an image and the step 320 of creating a modified image may be performed at the smartphone. The modified image may then be transmitted to the remote server, via a wireless data connection (e.g. wireless network or cellular data network). The step 330 of deriving the target specification may be performed at the server. Similarly, the step 350 of calculating the composition may be performed at the server. Once the composition has been calculated, the corresponding dye preparation may be made at a manufacturing facility and then sent by post to the customer who ordered it via the smartphone app.

In another example, the step 330 of deriving the target specification may be performed at the smartphone. In this case, there is no need to transmit the modified image to the remote server. Instead, the target specification is transmitted. This may require less data to be transferred and therefore it may be faster than uploading an image.

As those skilled in the art will appreciate, the division of labor between computing devices (such as a smart phone and a remote server) may be organized in other ways as well.

As those skilled in the art will appreciate, the smartphone discussed above is just one example of the kind of device that could be used in an embodiment. Other personal portable electronic devices could be used, including but not limited to, a laptop or notebook computer, and a tablet computing device. Preferably the personal portable electronic device has an integrated camera.

According to a further aspect of the invention, a computer program product is provided for programming a computer, personal portable electronic device, and/or remote server to implement embodiments of the invention.

In general, the various embodiments may be implemented in hardware or special purpose circuits, software, logic or any combination thereof. For example, some aspects may be implemented in hardware, while other aspects may be implemented in firmware or software which may be executed by a controller, microprocessor or other computing device, although these are not limiting examples. While various aspects described herein may be illustrated and described as block diagrams, flow charts, or using some other pictorial representation, it is well understood that these blocks, apparatus, systems, techniques or methods described herein may be implemented in, as non-limiting examples, hardware, software, firmware, special purpose circuits or logic, general purpose hardware or controller or other computing devices, or some combination thereof.

The embodiments described herein may be implemented by computer software executable by a data processor of the apparatus, such as in the processor entity, or by hardware, or by a combination of software and hardware. Further in this regard, it should be noted that any blocks of the logic flow as in the Figures may represent program steps, or interconnected logic circuits, blocks and functions, or a combination of program steps and logic circuits, blocks and functions. The software may be stored on such physical media as memory chips, or memory blocks implemented within the processor, magnetic media such as hard disk or floppy disks, and optical media such as for example DVD and the data variants thereof, or CD.

The memory may be of any type suitable to the local technical environment and may be implemented using any suitable data storage technology, such as semiconductor-based memory devices, magnetic memory devices and systems, optical memory devices and systems, fixed memory and removable memory. The data processors may be of any type suitable to the local technical environment, and may include one or more of general purpose computers, special purpose computers, microprocessors, digital signal processors (DSPs), application specific integrated circuits (ASIC), gate level circuits and processors based on multi-core processor architecture, as non-limiting examples.

Embodiments as discussed herein may be practiced in various components such as integrated circuit modules. The design of integrated circuits is by and large a highly automated process. Software tools are available for converting a logic level design into a semiconductor circuit design ready to be etched and formed on a semiconductor substrate. Programs, such as those provided by Synopsys, Inc. of Mountain View, Calif. and Cadence Design, of San Jose, Calif. automatically route conductors and locate components on a semiconductor chip using well established rules of design as well as libraries of pre-stored design modules. Once the design for a semiconductor circuit has been completed, the resultant design, in a standardized electronic format (e.g., Opus, GDSII, or the like) may be transmitted to a semiconductor fabrication facility or "fab" for fabrication.

A hair dye preparation designed using an embodiment of the invention may be mass produced for sale to many customers or may be prepared—for example in a hair salon—as a bespoke product for one individual customer.

A preparation according to an embodiment of the present invention may comprise various ingredients, as long as these are not excluded by the claims.

Suitable ingredients include, but are not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof. Suitable ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

The preparation may comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In one embodiment, the solvent may be selected from the group consisting of water, ethanol, propanol, isopropanol, glycerol, 1,2-propylene glycol, hexylene glycol, ethoxy diglycol, and mixtures thereof.

Typically, the preparation may comprise water as a main ingredient, particularly in a total amount ranging from at least about 50%, alternatively from at least about 60%, alternatively from at least about 70%, by weight of the total preparation. Typically, when present, the preparation comprises a total amount of organic solvents ranging from about 1% to about 30%, by weight of the total preparation.

The preparation may comprise at least one source of an oxidizing agent. Any oxidizing agent known in the art may be used. Preferred oxidizing agents are water-soluble peroxygen oxidizing agents. As used herein, "water-soluble" means that in standard conditions at least about 0.1 g, preferably about 1 g, more preferably about 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

Typically, the preparation may comprise a total amount of oxidizing agents ranging from about 0.1% to about 10%, alternatively from about 1% to about 9%, alternatively from about 1.5% to about 8%, by weight of the total preparation.

Suitable water-soluble oxidizing agents include, but are not limited to: inorganic peroxygen materials capable of yielding hydrogen peroxide in an aqueous solution.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

In a specific embodiment, the preparation comprises a water-soluble oxidizing agent selected from the group consisting of hydrogen peroxide, percarbonates (which may be used to provide a source of both oxidizing agent and carbonate ions and or ammonium ions), persulphates, and mixtures thereof.

When the preparation is obtained by mixing a developer and a tint prior to use, the oxidizing agent may be present in the developer. The developer may be based on any desired formulation chassis, including any commercial product, for example an oil-in-water emulsion. Typical developer compositions comprise about 6% or about 9% of the $H_2O_2$ relative to the total weight of the developer. A commercial example is the Welloxon® Emulsion with respectively about 6% and about 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

The preparation may comprise an alkalizing agent. Any alkalizing agent known in the art may be used.

Typically, the preparation may comprise a total amount of alkalizing agents ranging from about 0.1% to about 10%, alternatively from about 0.5% to about 6%, alternatively from about 1% to about 4%, by weight of the total preparation.

Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine. Preferably, if present, the ammonium ions and carbonate ions are present in the preparation at a weight ratio of from 3:1 to 1:10, alternatively from 2:1 to 1:5.

When the preparation is obtained by mixing a developer and a tint prior to use, the alkalizing agent is generally present in the tint.

The preparation may comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the preparation may comprise a total amount of oxidative dye precursors ranging up to about 12%, alternatively from about 0.01% to about 10%, alternatively from about 0.03% to about 8%, alternatively from about 0.05% to about 6%, by weight of the total preparation.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy] ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the preparation is obtained by mixing a tint and a developer, the primary intermediates and couplers are usually incorporated into the tint.

The preparation may comprise compatible direct dyes, in an amount sufficient to provide additional coloring, particularly with regard to intensity. Typically, the preparation may comprise a total amount of direct dyes ranging from about 0.005% to about 4%, by weight of the total preparation.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N- propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the preparation is obtained by mixing a tint and a developer, the direct dyes are usually incorporated into the tint.

The preparation may comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the preparation may comprise a total amount of chelants ranging from at least about 0.01%, alternatively from about 0.01% to about 5%, alternatively from about 0.25% to about 3%, alternatively from about 0.5% to about 1%, by weight of the total preparation.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative —$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the preparation comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the preparation is obtained by mixing a tint and a developer, the chelants may be incorporated in the tint and/or in the developer. A chelant is usually present in the developer for stability reasons.

The preparation may comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalizing agent and/or is present in an amount sufficient to reduce the damage to the hair during the coloring/bleaching process. Typically, the preparation may comprise a total amount of radical scavengers ranging from about 0.1% to about 10%, alternatively from about 1% by weight to about 7%, by weight of the total preparation. Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

The preparation may comprise, in addition to the alkalizing agent discussed above, a pH modifier and/or buffering agent in an amount that is sufficiently effective to adjust the pH of the preparation to fall within a range from about 3 to about 13, alternatively from about 8 to about 12, alternatively from about 9 to about 11. Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof. Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

The preparation may comprise a thickener in an amount sufficient to provide the preparation with a viscosity so that it can be readily applied to the hair without unduly dripping off the hair and causing mess. Typically, the preparation may comprise a total amount of thickeners ranging from at least about 0.1%, alternatively at least about 0.5%, alternatively at least about 1%, by weight of the total preparation. Suitable thickeners include, but are not limited to: associative polymers, polysaccharides, non-associative polycarboxylic polymers, and mixtures thereof. Further details of suitable thickeners may be found in WO 2013/126657, in particular at pages 14-18.

The preparation may comprise a source of carbonate ions, carbamate ions, hydrogen carbonate ions, and mixtures thereof in a sufficient amount to reduce damage to the hair during the coloring process.

Typically, the preparation may comprise a total amount of a carbonate ion source ranging from about 0.1% to about 15%, alternatively from about 0.1% to about 10%, alternatively from about 1% to about 7%, by weight of the total preparation.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

The preparation may comprise a conditioning agent, and/or be used in combination with a preparation comprising a conditioning agent.

Typically, the preparation may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total preparation. The conditioning agent may be included in a separate pre- and/or post-treatment preparation.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol. Further details of suitable conditioning agents may be found in WO 2013/126657, in particular at pages 20-26.

The preparation may comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

Typically, the preparation may comprise a total amount of surfactants ranging from about 1% to about 60%, alternatively from about 2% to about 30%, alternatively from about 8% to about 25%, alternatively from about 10% to about 20%, by weight of the total preparation.

The preparations may comprise a mixture of an anionic surfactant and an amphoteric surfactant with one or more nonionic surfactants. The preparation may comprise a total amount of anionic surfactant ranging from about 0.1% to about 20%, alternatively from about 0.1% to about 15%, alternatively from about 5% to about 15%, by weight of the total preparation; and a total amount of amphoteric and/or nonionic components, which may range independently from each other from about 0.1% to about 15%, alternatively from about 0.5% to about 10%, alternatively from about 1% to about 8%, by weight of the total preparation. Further details of suitable surfactants may be found in WO 2013/126657, in particular at pages 26-31.

The preparation may have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the preparation. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the preparation is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=\frac{1}{2}((2\times(+1)^2\times 0.050)+(+1)^2\times 0.020+(-2)^2\times 0.050+(-1)^2\times 0.020)=0.17$ M.

It is understood that the examples of methods of use and embodiments described herein are for illustrative purposes only and that various modifications or changes in light thereof will be suggested to one skilled in the art without departing from the scope of the present invention.

Retail oxidative hair dye preparations are usually sold in kits comprising, in individually packaged components such as separate containers, a dye component (also called "dye cream" for emulsions or "dye liquid" for solutions) comprising the oxidative dye precursors and alkalizing agent which is typically ammonia in a suitable carrier and; a oxidizing component (also called "hydrogen peroxide cream" for emulsions or "hydrogen peroxide liquid" for solutions) comprising the oxidizing agent (usually hydrogen peroxide). The consumer mixes the dye component and oxidizing component together immediately before use and applies it onto the hair. Similarly, retail bleaching preparations are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching preparations are obtained by mixing the above-mentioned preparations immediately before use.

For the professional hair salon market, the hair dye component and the oxidizing component and/or bleaching preparations are typically supplied independently to allow the professional to select a preferred combination.

After working the combined mixture for a few minutes (to insure uniform application to all of the hair), the oxidative dye preparation is allowed to remain on the hair for an amount sufficient for the dyeing to take place (usually from about 2 to about 60 minutes, typically about 30 to about 45 minutes). The consumer or salon professional then rinses the hair thoroughly with water and/or shampoo and allows it to dry. It will be observed that the hair has changed from its original color to the desired color.

In both retail and professional applications, an optional conditioning agent can also be provided. In this embodiment, all three preparations can be mixed immediately before use and applied together, or the conditioning agent can be applied (after an optional rinse step), as a post-treatment immediately after the oxidative dye preparation or bleaching preparation resulting from the mixture of the other containers.

The kits may also comprise as optional components a pre-treatment preparation and/or a color refresher preparation. Such color refresher preparations comprise at least one pre-formed dye and may be applied to the hair immediately after the oxidative color i.e. from about 1 minute after oxidative hair dye or bleach application to about 60 days after the application. These color refresher preparation can be used to increase the initial color obtained and or boost the color during the wash and style cycle until the next oxidative coloring or bleaching event.

The dye preparation and the oxidizing preparation may be, independently from one another, prepared as so called thin liquids or thicker type creams. Typically, thin type liquids have a viscosity of less than about 1000 cPs. Thick type creams typically have a viscosity greater than about 3000 cPs.

Upon mixing the dye and oxidizing preparations, the resultant hair coloring and/or bleaching preparation preferably has a viscosity of from about 1000 to about 60000 cPs, alternatively from about 2000 to about 30000 cPs, alternatively from about 3000 to about 25000 cPs. Viscosity is measured using Brookfield viscometers with cone and plate attachment. For viscosities in the range of about 0 to about 12000 cPs, the Brookfield DV-11 viscometer with S42 plate is used. 2 ml sample of the preparation is equilibrated at 26.7° C. for three minutes before the readings are taken at 1 rpm. For viscosities in the range of about 12,000 to about 60,000 cPs, the Brookfield DV-1 viscometer with S52 plate is used. 0.5 ml sample of the preparation is equilibrated for 1 minute at 26.7° C. before the readings are taken at 1 rpm.

The kits described hereinabove are well-known in the art and the preparations in each container can be manufactured utilizing any one of the standard approaches, these include a) 'Oil-in-water' process, b) 'Phase Inversion' process and c) 'One-pot' process. For example, when using "oil-in-water" process, surfactants are added to approximately 50% of total water amount of the preparation at about 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or coloring kit.

Preparations may be provided in a variety of packaging devices and/or dispensing devices. These dispensing devices can come in the form of separate devices which may be used independently or in combination with one another. Typically, the hair coloring or bleaching preparations are contained within separate single or multi compartment containers so that the preparations can be stored separately from one another before use. The preparations are then mixed together by a mixing means and then dispensed from the device and applied to the consumer's hair by an application means.

Alternatively the preparations may be provided in the form of foam which is applied to the hair. Foam formation is typically achieved by the use of a foaming agent incorporated within the mixed preparation (typically present in either the oxidizing preparation or the dye preparation or both) in combination with a manually operated foaming device. Such manually operated foaming devices are known in the art and include aerosols devices, squeeze foamers and pump foamers. Suitable foaming agents includes surfactants such as anionic, nonionic and amphoteric surfactants, nonionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

The hair coloring preparation may be obtained by mixing immediately prior to use a tint and a developer. A sufficient amount of the mixture is applied to the hair, according to the hair abundance, generally from about 60 to about 250 grams. The preparation is applied to the hair to be dyed and remains in contact with the hair for an amount of time effective to dye the hair. Typically, the hair dye preparation is allowed to act on the hair from about 2 to about 60, preferably about 15 to about 45, more preferably about 30 minutes, at a temperature ranging from 15° C. to about 50° C. Thereafter, the hair is rinsed with water to remove the preparation and dried. If necessary, the hair is washed with a shampoo and rinsed, e.g., with water or a weakly acidic solution, such as a citric acid or tartaric acid solution, and dried. Optionally, a separate conditioning product may also be provided.

The method of treating hair with the preparation may therefore comprise the steps of:

(i) providing a tint comprising the gel network thickening system and if present an alkalizing agent and oxidative precursor dyes and/or direct dyes;

(ii) providing a developer comprising an oxidizing agent;

(iii) mixing the developer with the tint to obtain a hair coloring preparation.

(iv) applying the preparation for the oxidative dyeing of keratin fibers onto the hair.

The glycerol can be comprised in the tint or the developer or distributed in both components. Typically glycerol will be at least comprised in the tint to serve as solvent for the dyes.

The method may further comprise waiting a period of time, typically between 2 minutes and 60 minutes, and then rinsing the hair coloring preparation from the hair. The hair coloring preparation can be applied on hair via applicator bottle or brush. It can be used on full head or partly on single strands (highlight application) as common highlight applicator foils, caps and special applicators can be used, but also freehand techniques such as balayage, with brush and/or combs can be possible. The preparation can also be applied as a mousse via a manual spray, a pressurized container or an aerosol mousse. The preparation may be dispensed as a solid form to which water is added to generate the oxidant and form a thickened vehicle suitable for hair coloring.

Coloring preparations, and the corresponding tint and developer, may be manufactured by conventional processes known in the art for manufacturing oxidative dyeing products, and ad-mixing the ingredients of each preparation in suitable vessels, followed by packaging in appropriate individual containers. The components may be for example packaged in plastic or aluminium bottles.

In particular, a kit may be provided comprising different components to be mixed by the consumer or salon stylist to obtain a hair dyeing preparation. Such a kit may comprise a tint comprising and a developer as indicated above.

The kit may be presented in a single package comprising separate containers for the tint, the developer, and optionally a conditioner, a color refresher or other hair treatment product, instructions for use, gloves. The instructions for use include the steps of the method described above and optionally provide visual cues or pictures for the desired steps of the method. Kits are usually sold in retail products with enough material in each component for preparing a hair dyeing preparation for one use.

The preparation may be dispensed as a foam using for example manually-actuable, non-aerosol dispenser such as a pump or squeeze foamers, aerosol mousse. See for example EP 613,728 B1, WO 97/013585 A1, EP 1,716,933A1, U.S. Pat. Nos. 3,709,437, 3,937,364, 4,022,351, 4,147,306, 4,184,615, 4,615,467 and FR 2,604,622. One particular example of a squeeze foamer useful herein is able to dispense from an upright or inverted position such as the one discussed in U.S. Pat. No. 6,604,693 assigned to Taplast, and more specifically, at column 2, line 65, through column 4, line 67 of that patent.

The preparation may also be dispensed as a solid form to which water is added to generate the oxidant and form a thickened vehicle suitable for hair coloring.

In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The embodiments may be implemented by means of hardware comprising several distinct elements. In a device claim enumerating several means, several of these means may be embodied by one and the same item of hardware. The mere fact that certain measures are recited in mutually different dependent claims does not indicate that a combination of these measures cannot be used to advantage. Furthermore in the appended claims lists comprising "at least one of: A; B; and C" should be interpreted as (A and/or B) and/or C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of calculating a composition for a preparation for treating hair fibers, the method comprising:
    obtaining a first image of hair fibers;
    providing a second computational model describing an interaction of light with hair fibers;
    obtaining, for the first image, a first set of hair fiber optical parameters, which describes the hair fibers in the first image;
    modifying the first set of fiber optical parameters, to produce a second set of hair fiber optical parameters describing a plurality of modified hair fibers;
    simulating, using the second computational model and the second set of hair fiber optical parameters, how light would interact with the modified hair fibers;
    rendering, based on a result of the simulation, a first synthetic image showing an appearance of the modified hair fibers; and
    providing said first synthetic image as the modified image;
    creating, based on the first image, a modified image illustrating a desired appearance of the hair fibers;
    deriving a target specification, based on at least one of: the modified image; and a modification performed to the first image to create the modified image, wherein the target specification comprises one or more numerical parameters defining the desired appearance of the hair fibers;

providing a first computational model that relates a composition of a preparation to a predicted appearance of the hair fibers when treated by that preparation; and calculating, using the first computational model and the target specification, a composition for the preparation that is predicted to produce, if the hair fibers are treated with the preparation, an appearance similar or identical to the desired appearance.

2. The method of claim 1, wherein each of the first and second sets of hair fiber optical parameters comprises parameters for at least three of the following four components:
- a first backward scattering component, describing how incident light is reflected from a first surface of a hair fiber;
- a first forward scattering component, describing how incident light is transmitted through the first surface of the hair fiber and a second surface of the hair fiber;
- a second backward scattering component, describing how incident light is transmitted through the first surface of the hair fiber, reflected from the second surface of the hair fiber, and transmitted through a third surface of the hair fiber; and
- an absorption component, describing how incident light is absorbed by the hair fiber.

3. The method of claim 1, wherein obtaining the first set of hair fiber optical parameters comprises:
- processing the first image to determine a set of estimated hair fiber optical parameters;
- simulating, using the second computational model and the estimated hair fiber optical parameters, how light would interact with hair fibers with the estimated parameters;
- computing an error metric comparing the result of the simulation with a content of the first image;
- updating the estimated hair fiber optical parameters, based on the error metric;
- iterating steps of simulating, computing, and updating, until the estimated hair fiber optical parameters converge to stable values; and
- determining the first set of fiber optical parameters based on the converged estimated fiber optical parameters.

4. The method of claim 1, wherein the target specification comprises a target color vector and wherein deriving the target color vector comprises:
- storing a plurality of sets of hair fiber optical parameters, each set describing real hair fibers of a different shade, and each set being associated with a color vector that was has been directly measured from the real hair fibers of that shade;
- identifying, among the stored sets of hair fiber optical parameters, the set that is most similar to the second set of hair fiber optical parameters, this set being designated as the nearest-neighbour set, the corresponding hair fibers being designated as the nearest neighbour hair fibers, and the associated color vector being designated as the nearest neighbour measured color vector;
- simulating, using the second computational model and the nearest-neighbour set of hair fiber optical parameters, how light would interact with the nearest neighbour hair fibers;
- rendering, based on the result of the simulation, a nearest neighbour synthetic image showing the appearance of a nearest neighbour hair fibers;
- deriving a nearest neighbour synthetic color vector from the nearest neighbour synthetic image;
- deriving a modified image color vector based on the modified image;
- calculating a color difference between the nearest neighbour synthetic color vector and the modified image color vector; and
- deriving the target color vector based on the nearest neighbour measured color vector and said color difference.

5. The method of claim 1, wherein the preparation comprises a plurality of dye compounds of one type present in respective dosages and wherein, calculating the composition using the first computational model, the dosages of all of the dye compounds of said type in the preparation are variable independently of one another, wherein said type is one of: primary dye compounds; coupler dye compounds; and direct dye compounds.

6. The method of claim 1, wherein calculating the composition using the first computational model comprises:
- calculating a plurality of candidate compositions, each of which is predicted to produce in the hair fibers an appearance similar or identical to the desired appearance; and
- choosing one of the candidate compositions, based on a criterion other than similarity to the target specification.

7. The method of claim 6, wherein the criterion comprises at least one, or any combination of two or more, of:
- a cost of manufacturing the preparation;
- a toxicological profile of ingredients within the preparation;
- a permanence of a result of treatment by the preparation, in particular a resistance to degradation due to at least one of: light at visible wavelengths, ultra-violet light, sweat, and water;
- a solubility of the preparation;
- an ionic strength of the preparation;
- a rheology of the preparation;
- a stability of the preparation;
- a coverage of the preparation on grey hair;
- an extent to which the preparation will stain skin during treatment;
- an ability of the preparation to deliver uniform color from a root to a tip of hair fibers;
- an ability to tailor the penetration depth of the color delivered by the preparation; and
- a shine after application of the preparation.

8. The method of claim 1, wherein the method further comprises:
- before calculating the composition using the first computational model, receiving one or more constraints on the composition; and
- calculating the composition, calculating a composition that satisfies the one or more constraints.

9. The method of claim 1, further comprising:
- making a preparation having the calculated composition;
- treating a sample of hair fibers with the preparation;
- comparing the treated hair fibers with at least one of: the target specification, and the modified image;
- modifying the target specification based on a result of the comparison; and
- calculating, using the first computational model and the modified target specification, a modified composition for the preparation.

10. The method of claim 1, wherein the first computational model includes at least one, or any combination of two or more, of:

a computational component that describes mass transport of a preparation into hair fibers;

a computational component that relates time-dependent concentrations of chemical species in a preparation to the initial composition of the preparation;

a computational component that relates time-dependent concentrations of chemical species in hair fibers to time-dependent concentrations of chemical species in the preparation; and a computational component that relates concentrations of chemical species to a reflectance spectrum of hair fibers.

11. The method of claim 1, wherein the target specification comprises one of:

a three-dimensional vector specifying a color in a three dimensional color space; and a reflectance spectrum.

12. The method of claim 1, wherein the preparation comprises a hair dye and the desired appearance of the hair fibers is a desired color.

13. One or more processor-readable storage devices containing processor readable code for programming one or more processors to perform a method according to claim 1 wherein the one or more storage devices are non-transitory.

14. A method of making a preparation for treating hair fibers, the method comprising:

calculating a composition of the preparation according to the method of claim 1;

followed by making the preparation having the calculated composition.

15. A method of calculating a composition for a preparation for treating hair fibers, the method comprising:

obtaining a target specification, comprising one or more numerical parameters defining a desired appearance of the hair fibers;

providing a second computational model describing an interaction of light with hair fibers;

obtaining, for the first image, a first set of hair fiber optical parameters, which describes the hair fibers in the first image;

modifying the first set of fiber optical parameters, to produce a second set of hair fiber optical parameters describing a plurality of modified hair fibers;

simulating, using the second computational model and the second set of hair fiber optical parameters, how light would interact with the modified hair fibers;

rendering, based on a result of the simulation, a first synthetic image showing an appearance of the modified hair fibers; and providing said first synthetic image as the modified image;

providing a first computational model that relates a chemical composition of the preparation to a predicted appearance of the hair fibers when treated by that preparation; and calculating, using the first computational model and the target specification, a composition for the preparation that is predicted to produce in the hair fibers an appearance similar or identical to the desired appearance, wherein the preparation comprises a plurality of dye compounds of one type present in respective dosages and wherein, in calculating the composition using the first computational model, the dosages of all of the dye compounds of that type in the preparation are variable independently of one another, wherein said type is one of: primary dye compounds; coupler dye compounds; and direct dye compounds.

* * * * *